(12) United States Patent
Vestgaarden

(10) Patent No.: US 11,819,226 B2
(45) Date of Patent: Nov. 21, 2023

(54) TOOL AND METHOD FOR IMPLANTING FUSION DEVICE INTO SACROILIAC JOINT

(71) Applicant: VGI Medical, LLC, Largo, FL (US)

(72) Inventor: Tov Inge Vestgaarden, Madeira Beach, FL (US)

(73) Assignee: VGI Medical, LLC, Largo, FL (US)

( * ) Notice: Subject to any disclaimer, the term of this patent is extended or adjusted under 35 U.S.C. 154(b) by 0 days.

(21) Appl. No.: 15/889,587

(22) Filed: Feb. 6, 2018

(65) Prior Publication Data

US 2019/0021748 A1 Jan. 24, 2019

Related U.S. Application Data

(63) Continuation of application No. 13/790,416, filed on Mar. 8, 2013, now Pat. No. 9,883,874.

(51) Int. Cl.
*A61B 17/17* (2006.01)
*A61B 17/88* (2006.01)
(Continued)

(52) U.S. Cl.
CPC .......... *A61B 17/1739* (2013.01); *A61B 17/17* (2013.01); *A61B 17/1757* (2013.01);
(Continued)

(58) Field of Classification Search
CPC .... A61F 2/4603; A61F 2/4611; A61F 2/4612; A61F 2/4614; A61F 2002/4615;
(Continued)

(56) References Cited

U.S. PATENT DOCUMENTS

| 4,441,492 A | 4/1984 | Rydell et al. |
| 5,609,636 A | 3/1997 | Kohrs et al. |
| (Continued) | | |

FOREIGN PATENT DOCUMENTS

| WO | WO 2008/153732 | 12/2008 |
| WO | WO 2011/087912 | 7/2011 |
| WO | WO 2012/054596 | 4/2012 |

OTHER PUBLICATIONS

Extended European Searh Report in connection with European Application No. 12833016, dated May 28, 2015.
(Continued)

*Primary Examiner* — Amy R Sipp
(74) *Attorney, Agent, or Firm* — Pandiscio & Pandiscio

(57) ABSTRACT

Tools for positioning an implant into the sacroiliac joint. A directional cannula includes a main body having a bore that receives the implant. A cut-out, allowing access to the joint, is formed in a leading end of the main body. A pair of parallel prongs extend from the leading end of the main body in transversely spaced apart relation to one another. A drill guide has a main body of rectangular transverse cross-section and a cylindrical head formed integrally with the main body. A transverse width-reducing step is formed in the main body near its distal end. First and second bores are formed in the cylindrical head and in the main body. Both bores are eccentric relative to the drill guide longitudinal axis of symmetry. The drill guide is rotated 180° after first and second drilling operations, prior to third and fourth drilling operations.

5 Claims, 31 Drawing Sheets

(51) Int. Cl.
  *A61F 2/46* (2006.01)
  *A61B 17/70* (2006.01)
  *A61B 17/90* (2006.01)
(52) U.S. Cl.
  CPC ........ *A61B 17/8894* (2013.01); *A61F 2/4603* (2013.01); *A61F 2/4611* (2013.01); *A61B 17/7055* (2013.01); *A61B 17/90* (2021.08)
(58) Field of Classification Search
  CPC ............. A61F 2002/4635; A61B 17/17; A61B 17/1714; A61B 17/1717; A61B 17/1739; A61B 17/1757; A61B 2017/90
  See application file for complete search history.

(56) References Cited

U.S. PATENT DOCUMENTS

| | | | |
|---|---|---|---|
| 5,683,394 | A | 11/1997 | Rinner |
| 6,113,602 | A | 9/2000 | Sand |
| 6,197,033 | B1 * | 3/2001 | Haid, Jr. ............ A61B 17/1757 606/279 |
| 6,200,322 | B1 * | 3/2001 | Branch ................ A61F 2/4611 606/104 |
| 6,402,785 | B1 | 6/2002 | Zdeblick et al. |
| 7,621,938 | B2 | 11/2009 | Molz, IV |
| 7,648,509 | B2 | 1/2010 | Stark |
| 7,674,296 | B2 | 3/2010 | Rhoda et al. |
| 7,691,148 | B2 | 4/2010 | Michelson |
| 7,708,761 | B2 | 5/2010 | Petersen |
| 7,758,648 | B2 | 7/2010 | Castleman et al. |
| D623,298 | S | 9/2010 | Thomas et al. |
| 7,850,736 | B2 | 12/2010 | Heinz |
| 7,918,891 | B1 | 4/2011 | Curran et al. |
| 8,157,842 | B2 | 4/2012 | Phan et al. |
| 8,162,981 | B2 | 4/2012 | Vestgaarden |
| 8,348,950 | B2 | 1/2013 | Assell et al. |
| 8,454,618 | B2 | 6/2013 | Stark |
| 8,623,053 | B2 | 1/2014 | Vestgaarden |
| 8,808,377 | B2 | 8/2014 | Donner |
| 8,882,818 | B1 | 11/2014 | Vestgaarden |
| 9,017,407 | B2 | 4/2015 | Donner |
| 9,375,243 | B1 | 6/2016 | Vestgaarden |
| 9,452,065 | B1 | 9/2016 | Lawson |
| 9,808,346 | B2 | 11/2017 | Stark |
| 9,883,874 | B1 | 2/2018 | Vestgaarden |
| 9,895,176 | B2 | 2/2018 | Vestgaarden |
| 10,463,504 | B2 | 11/2019 | Vestgaarden |
| 2002/0077641 | A1 | 6/2002 | Michelson |
| 2002/0082701 | A1 * | 6/2002 | Zdeblick ............ A61B 17/1757 623/17.16 |
| 2003/0032962 | A1 | 2/2003 | McGahan et al. |
| 2004/0059337 | A1 | 3/2004 | Hanson et al. |
| 2004/0260286 | A1 | 12/2004 | Ferree |
| 2005/0149192 | A1 | 7/2005 | Zucherman et al. |
| 2005/0159813 | A1 | 7/2005 | Molz, IV |
| 2006/0054171 | A1 | 3/2006 | Dall |
| 2006/0085068 | A1 | 4/2006 | Barry |
| 2006/0111782 | A1 | 5/2006 | Petersen |
| 2007/0010889 | A1 | 1/2007 | Francis |
| 2007/0050033 | A1 | 3/2007 | Reo et al. |
| 2007/0083265 | A1 | 4/2007 | Malone |
| 2007/0118224 | A1 | 5/2007 | Shah et al. |
| 2008/0132949 | A1 | 6/2008 | Aferzon et al. |
| 2008/0154305 | A1 | 6/2008 | Foley et al. |
| 2008/0154374 | A1 | 6/2008 | Labrom |
| 2008/0183211 | A1 | 7/2008 | Lamborne et al. |
| 2008/0208344 | A1 | 8/2008 | Kilpela et al. |
| 2008/0255666 | A1 | 10/2008 | Fisher et al. |
| 2009/0012527 | A1 | 1/2009 | Mignucci et al. |
| 2009/0036927 | A1 | 2/2009 | Vestgaarden |
| 2009/0062858 | A1 | 3/2009 | Dziedzic et al. |
| 2009/0069816 | A1 | 3/2009 | Sasing et al. |
| 2009/0187247 | A1 | 7/2009 | Metcalf, Jr. et al. |
| 2009/0216238 | A1 | 8/2009 | Stark |
| 2009/0234389 | A1 | 9/2009 | Chuang et al. |
| 2009/0259261 | A1 | 10/2009 | Reiley |
| 2010/0076443 | A1 | 3/2010 | Bertagnoli et al. |
| 2010/0241166 | A1 | 9/2010 | Dwyer et al. |
| 2010/0318127 | A1 | 12/2010 | Phan et al. |
| 2010/0324683 | A1 | 12/2010 | Reichen et al. |
| 2011/0166600 | A1 | 7/2011 | Lamborne et al. |
| 2012/0004729 | A1 | 1/2012 | Zipnick |
| 2012/0101582 | A1 | 4/2012 | Raiszadeh et al. |
| 2012/0197263 | A1 | 8/2012 | Copf et al. |
| 2012/0221051 | A1 | 8/2012 | Robinson |
| 2012/0239089 | A1 | 9/2012 | Druma et al. |
| 2013/0282128 | A1 | 10/2013 | McKay |
| 2014/0200668 | A1 * | 7/2014 | Kirschman .......... A61B 17/025 623/17.16 |
| 2014/0324103 | A1 | 10/2014 | Levieux et al. |
| 2014/0336763 | A1 | 11/2014 | Donner et al. |
| 2016/0367379 | A1 | 12/2016 | Refai |

OTHER PUBLICATIONS

International Search Report and Written Opinion of the International Searching Authority issued in connection with International (PCT) Patent Application No. PCT/US2012/056304, dated Feb. 26, 2013.

McGuire, R. et al., Dual fibular allograft dowel technique for sacroiliac jointt arthrodesis, Evidence-Based Spine-Care Journal, vol. 3, No. 3, 2012, pp. 21-28.

Stein, M. et al., Young Investigator Award: Percutaneous Facet Joint Fusion: Preliminary Experience, Journal of Vascular and Interventional Radiology, vol. 4, No. 1, Jan. 1993, pp. 69-74.

VGI Medical, LLC, Surgical Technique Guide, 2013.

* cited by examiner

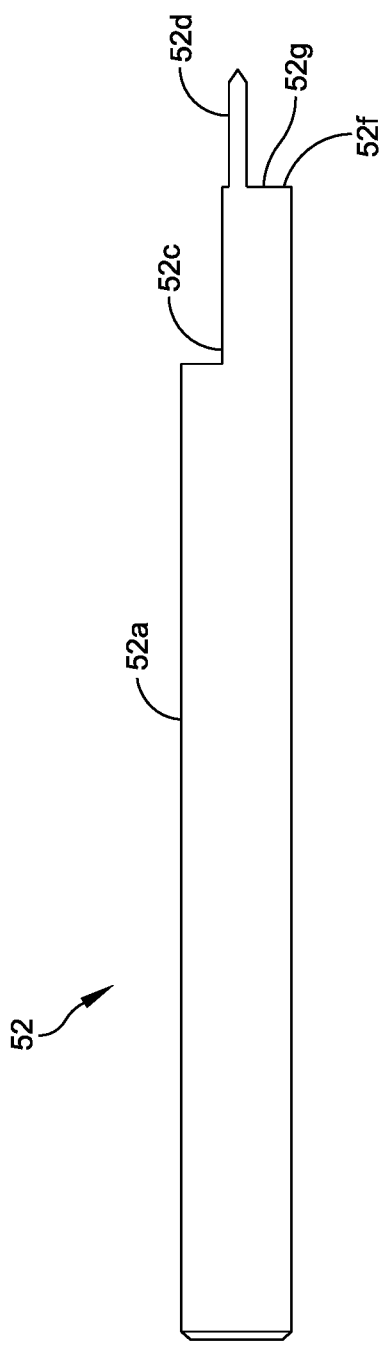

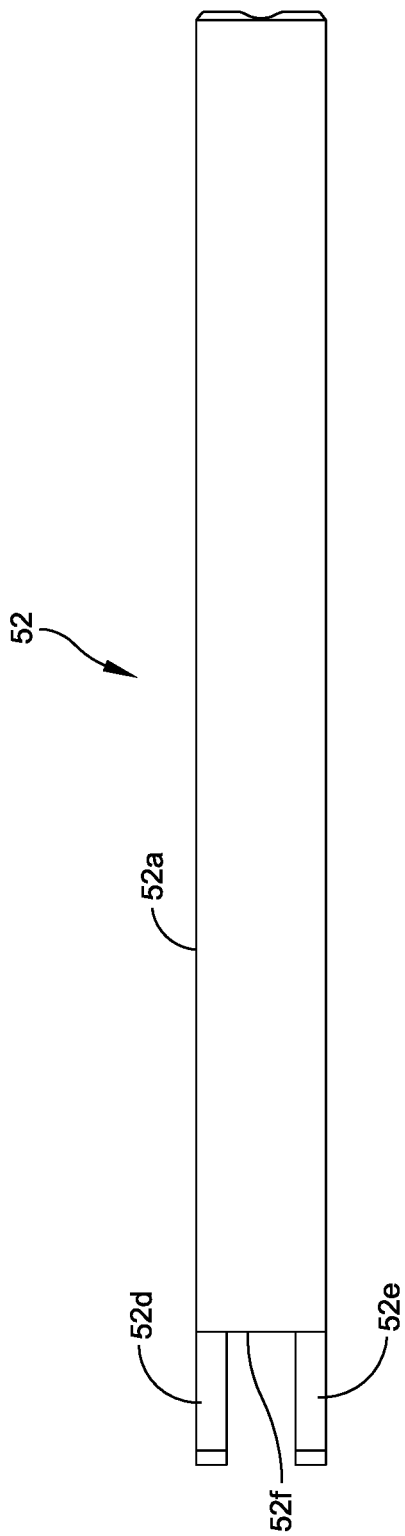

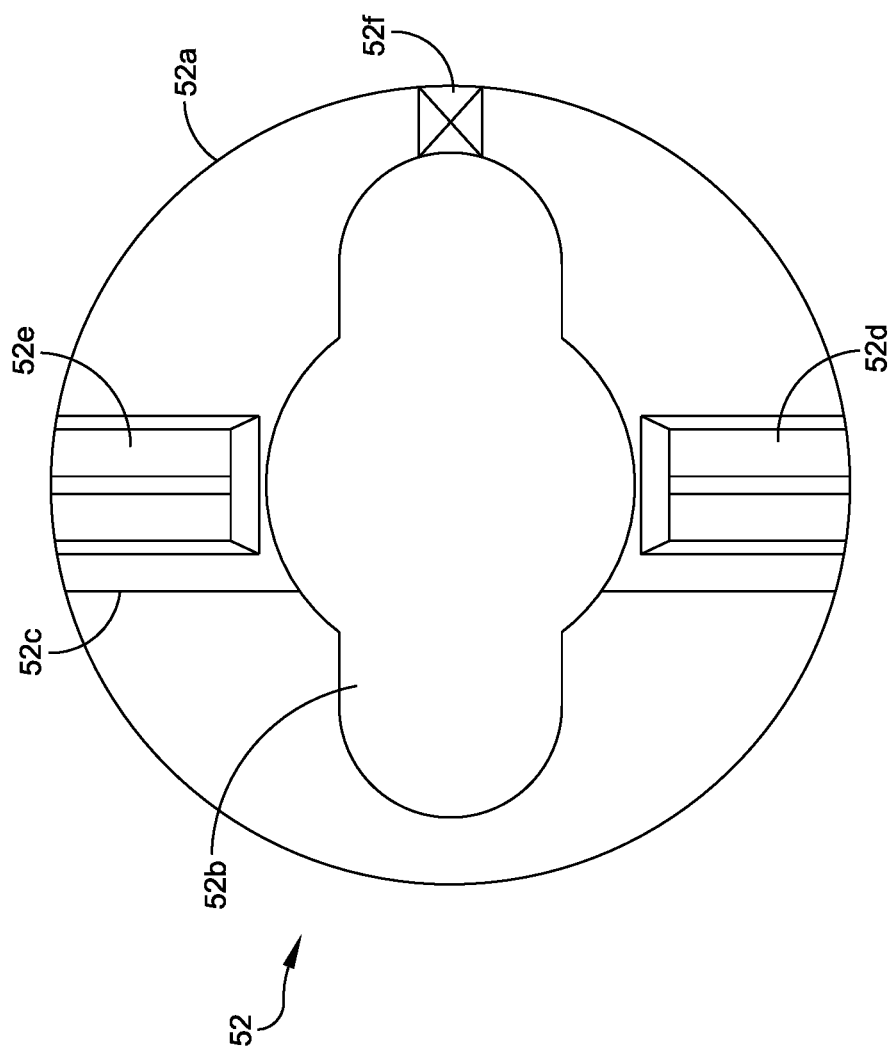

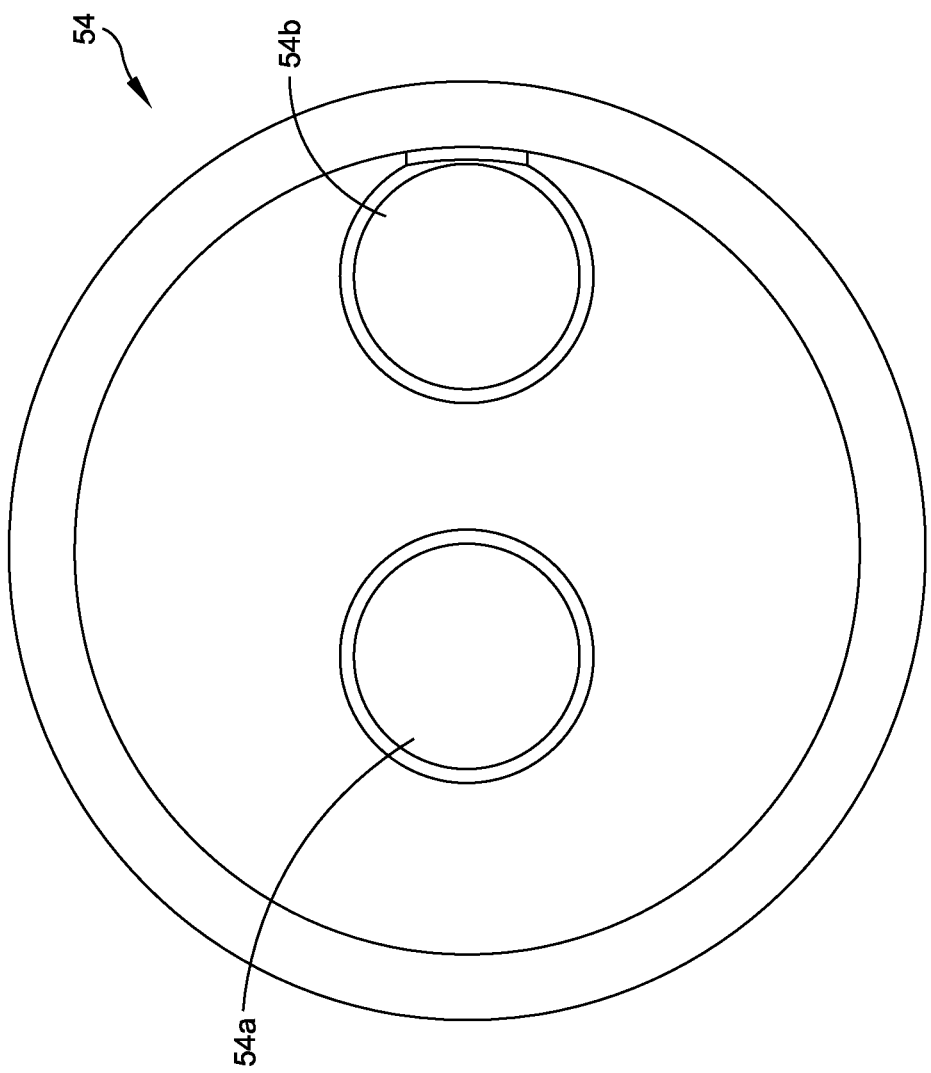

TOOL AND METHOD FOR IMPLANTING FUSION DEVICE INTO SACROILIAC JOINT

REFERENCE TO PENDING PRIOR PATENT APPLICATION

This patent application is a continuation of pending prior U. S. Patent Application Ser. No. 13/790,416, filed Mar. 8, 2013 by VG Innovations, LLC for TOOL AND METHOD FOR IMPLANTING FUSION DEVICE INTO SACROILIAC JOINT, which patent application is hereby incorporated herein by reference.

BACKGROUND OF THE INVENTION

1. Field of the Invention

This invention relates, generally, to surgical instruments and methods. More particularly, it relates to a tool for introducing a fusion device, also known as an implant or fusion implant, into a sacroiliac joint.

2. Description of the Prior Art

Placing a fusion implant into the sacroiliac area is difficult because the ilium protrudes and blocks easy access to the site. Part of the ilium can be cut and removed to improve access, but such cutting weakens the ilium, extends the time required for surgery and recovery from surgery, and increases the patient's pain.

New tools are needed that would eliminate the need to cut the ilium.

However, in view of the art considered as a whole at the time the present invention was made, it was not obvious to those of ordinary skill in the art how the needed tools could be provided.

SUMMARY OF THE INVENTION

The long-standing but heretofore unfulfilled need for a device that facilitates the insertion of an implant into the sacroiliac joint is now met by a new, useful, and non-obvious invention.

The inventive structure includes a directional cannula having a main body of elongate cylindrical extent. A bore having the shape of a spinal fusion implant is formed in the main body. That bore is also configured to receive a drill guide therein, if needed.

A cut-out is formed in a leading end of the main body by a radial cut, i.e., a cut that is normal to a longitudinal axis of said main body. The radial cut extends less than half-way through the main body. The cut-out is also formed by a second longitudinally-extending cut that extends from a leading end of the main body to the radial cut at a point of deepest penetration of the radial cut.

The implant is captured within the bore even when the implant travels to the cut-out or notch formed in the main body and is exposed to view. Since the notch has a radial depth less than the diameter of the bore, the implant is more than half-surrounded by the lumen and cannot fall therefrom.

A pair of parallel prongs extends longitudinally from the leading end of the main body in transversely spaced apart relation to one another. The prongs are adapted to enter the sacroiliac joint, which is the space between the ilium and sacrum.

The novel drill guide includes an elongate main body having a rectangular transverse cross-section, an enlarged cylindrical head formed integrally with the main body at a proximal end of the main body, and a transverse width-reducing step formed in the main body near a distal end of the main body.

A first longitudinally-extending bore is formed in the enlarged cylindrical head and in the main body. The first bore is eccentric relative to a longitudinal axis of symmetry of the drill guide.

A second longitudinally-extending bore is also formed in the enlarged cylindrical head and in the main body. The second bore is also eccentric relative to the longitudinal axis of symmetry of the drill guide and the second bore is parallel to the first bore.

A drill bit is sequentially placed within the first and second bores to create clearance space in the ilium when the drill guide is received within the bore of the directional cannula. The drill guide is then removed from the bore of the directional cannula, rotated one hundred eighty degrees (180°), and the drill bit is again sequentially placed within the first and second bores to create clearance space in the sacrum.

An important object of this invention is to facilitate the implanting of a fusion implant in the sacroiliac area.

A more specific object is to accomplish the first object in the absence of removing substantial parts of the ilium.

Another important object is to provide tools that produce consistent results from patient to patient.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the nature and objects of the invention, reference should be made to the following detailed disclosure, taken in connection with the accompanying drawings, in which:

FIG. 7C is a side elevational view of the directional cannula of FIG. 7A;

FIG. 7D is a bottom plan view of the directional cannula of FIG. 7A;

FIG. 7E is an end view of the leading end of the directional cannula of FIG. 7A;

FIG. 8D is an end elevational view of the trailing end of the drill guide of FIG. 8A;

DETAILED DESCRIPTION OF THE PREFERRED EMBODIMENT

Figure 1A:
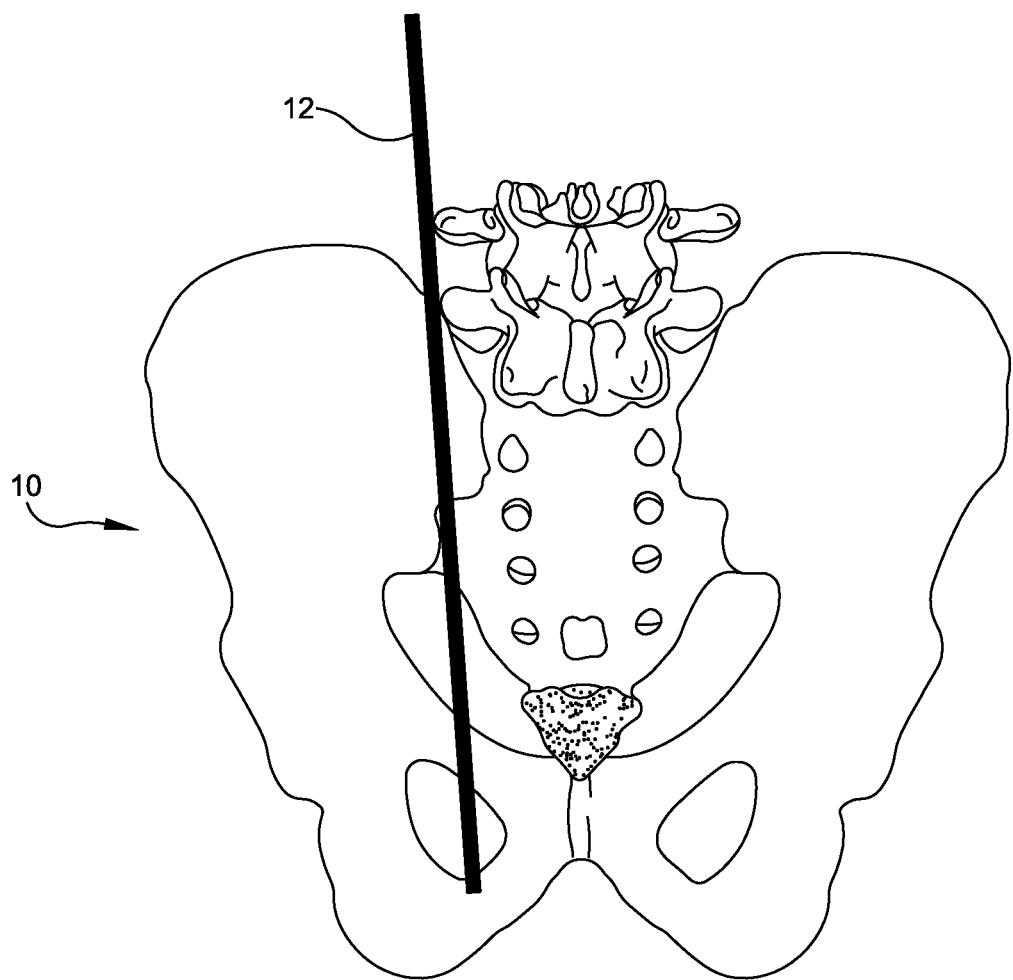
FIG. 1A is an X-ray view depicting the first guide wire placed on the skin to identify the location of the sacroiliac joint.

FIGS. 1A-8D depict an illustrative embodiment of the novel instrument and the novel method steps with which it is used. The sacroiliac (SI) joint of a patient is denoted as a whole by the reference numeral 10.

The novel method steps include the steps of taking anterior, posterior, and lateral X-ray views of the sacroiliac (SI) area to identify the anatomy that is causing pain in a patient.

An entry point is established to gain access to the SI joint with an oblique (approximately thirty five degree (35°) angle) and a Ferguson angle measurement of curvature which is approximately ten to fifteen degrees (10-15°).

Figure 1B:
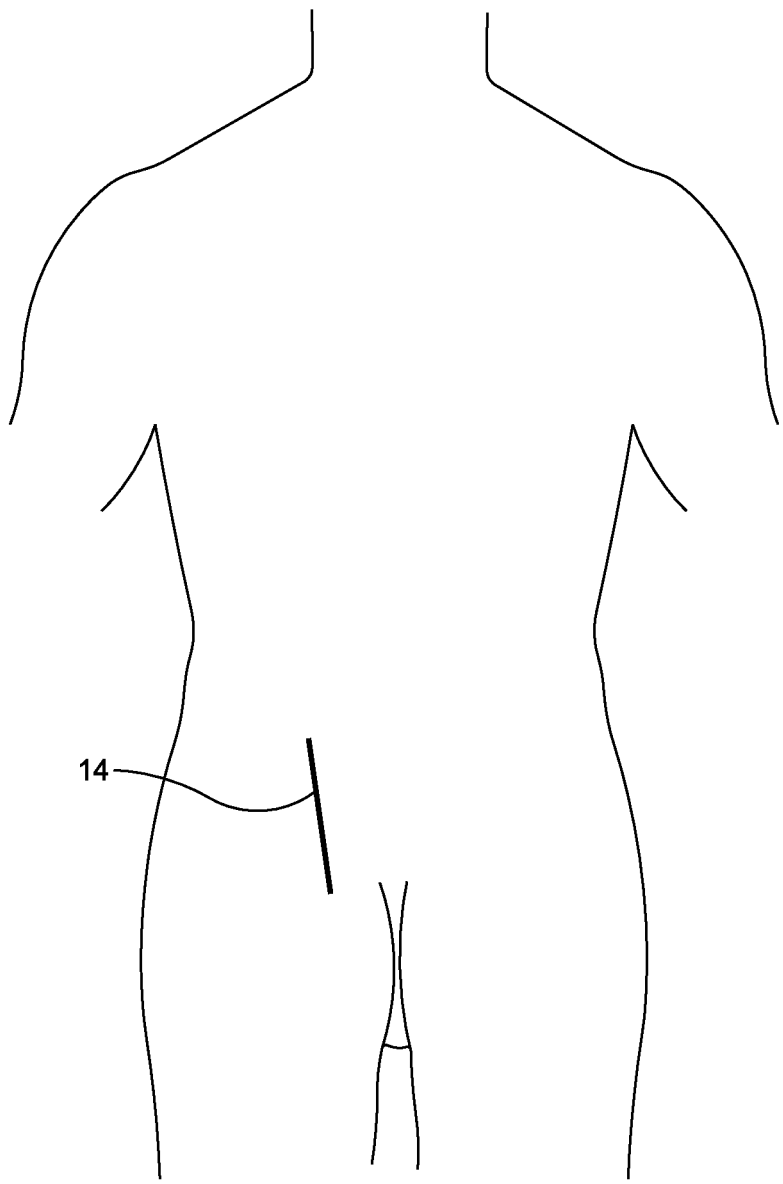
FIG. 1B is a diagrammatic view of a mark made on a patient's skin to indicate the position of the guide wire used to locate the sacroiliac joint in FIG. 1A.

As depicted in FIG. 1A, first guide wire 12 is placed on top of the SI joint and as depicted in FIG. 1B, the patient's skin is marked with a first straight line 14 to indicate the position of first guide wire 12. First straight line 14 is drawn through SI joint 10 from the superior position of the joint to the inferior position of the joint.

Figure 2A:
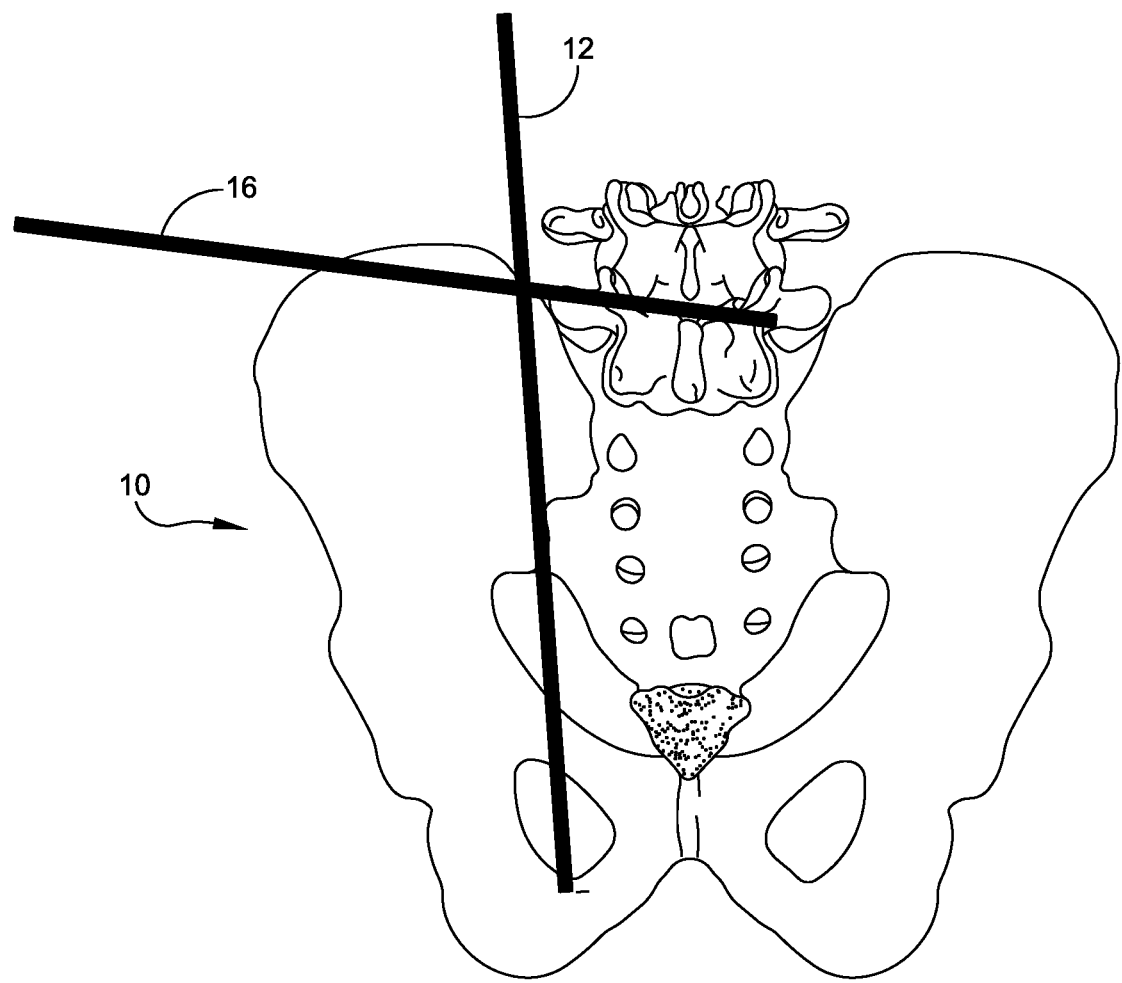
FIG. 2A is an X-ray view depicting the second guide wire placed on the skin to identify the superior portion of the sacroiliac joint.
Figure 2B:
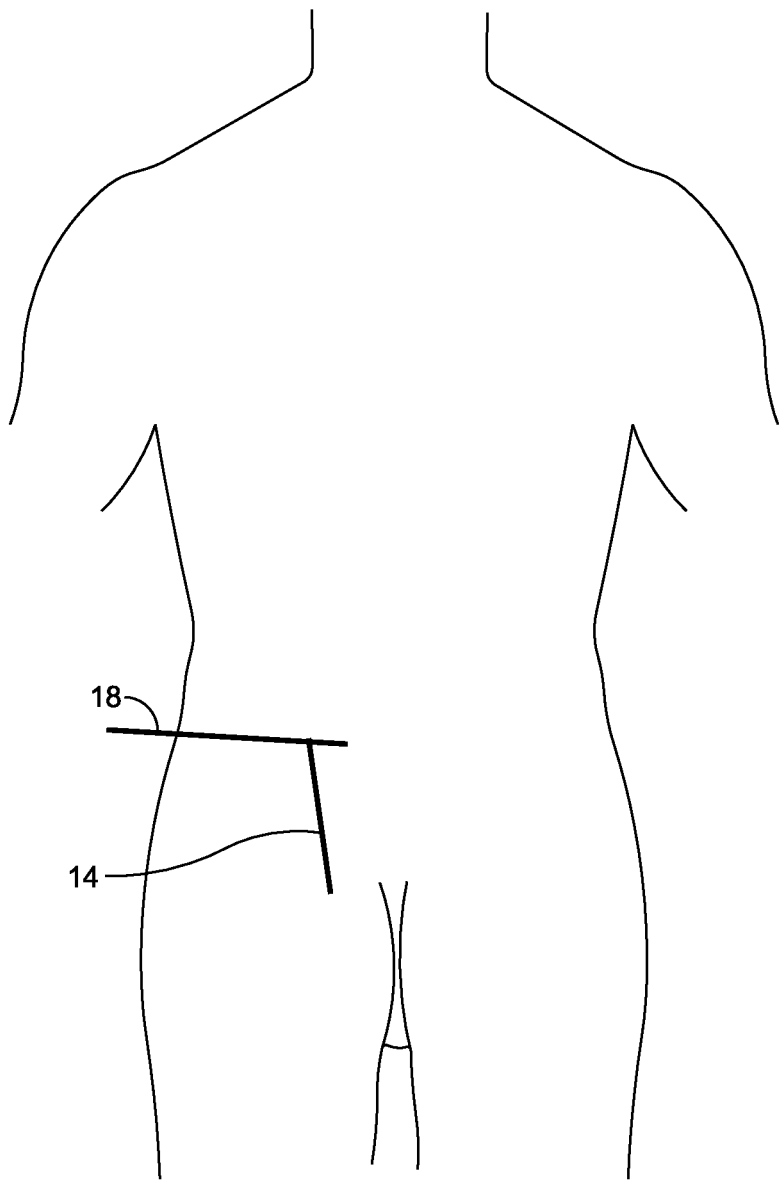
FIG. 2B is a diagrammatic view of a mark made on a patient's skin to indicate the position of the guide wire used to identify the superior portion of the sacroiliac joint in FIG. 2A.

As depicted in FIG. 2A, a second guide wire 16 is then placed over the superior section of joint 10 in intersecting relation to first guide wire 12. As depicted in FIG. 2B, the patient's skin is marked with a second straight line 18 to indicate the position of second guide wire 16.

Figure 3A:
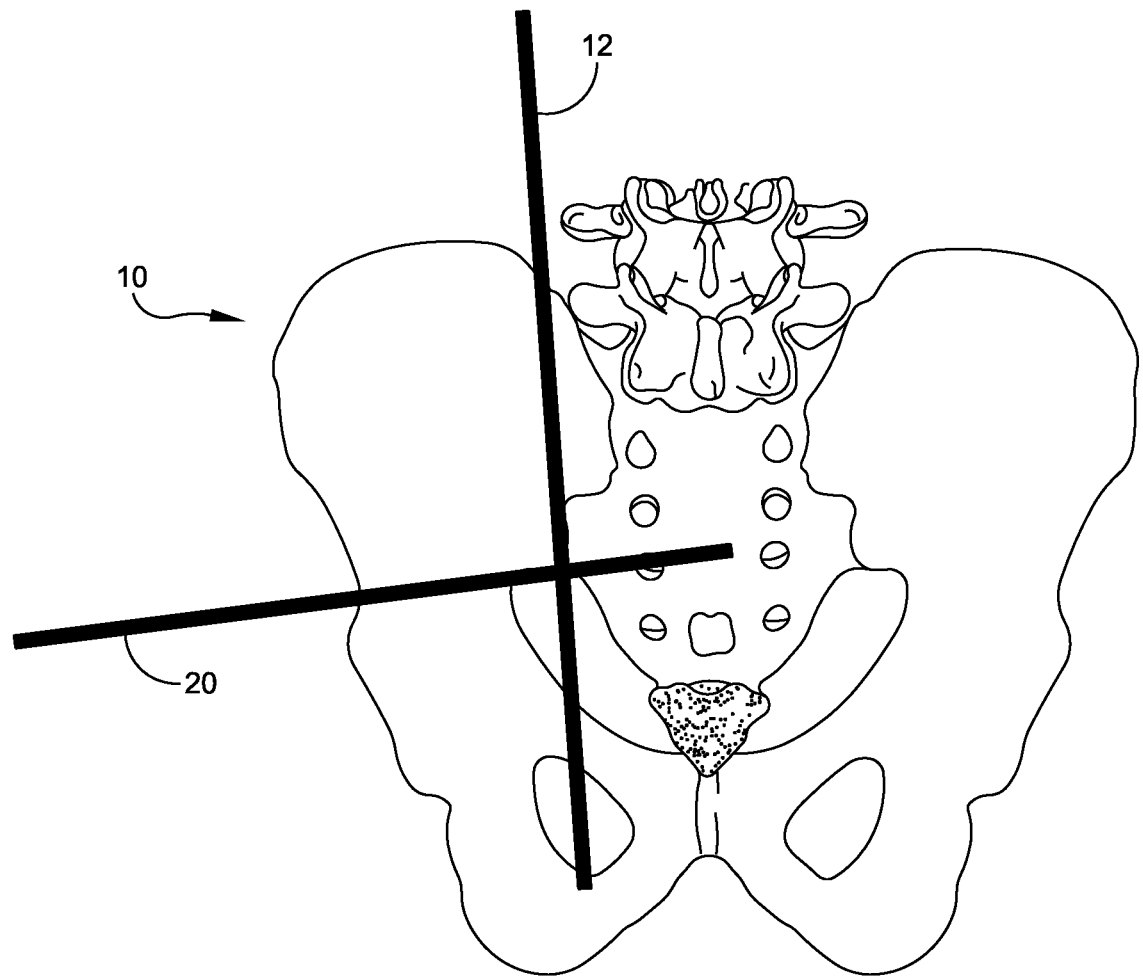
FIG. 3A is an X-ray view depicting the third guide wire placed on the skin to identify the inferior portion of the sacroiliac joint.
Figure 3B:
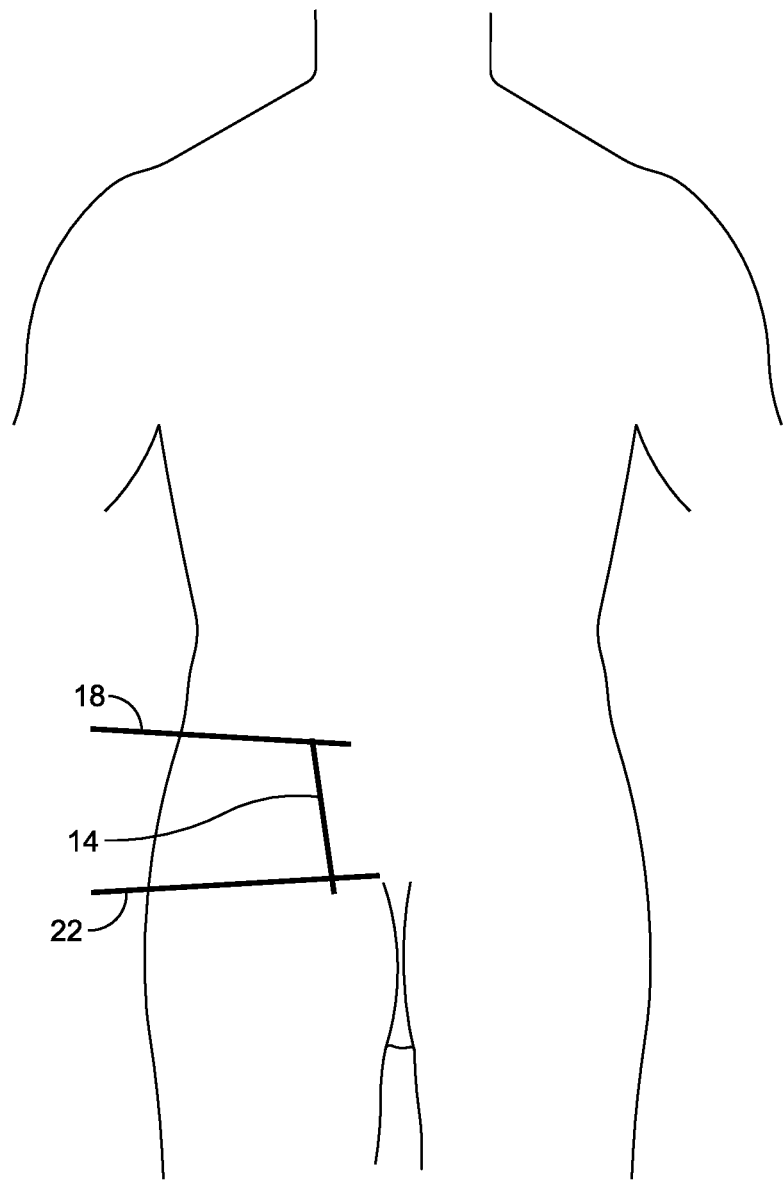
FIG. 3B is a diagrammatic view of a mark made on a patient's skin to indicate the position of the guide wire used to identify the inferior portion of the sacroiliac joint in FIG. 3A.

A third guide wire 20, as depicted in FIG. 3A, is then placed over the inferior section of the joint in intersecting relation to first guide wire 12. The patient's skin, as depicted in FIG. 3B, is marked with a third straight line 22 to indicate the position of third guide wire 20.

Figure 4:
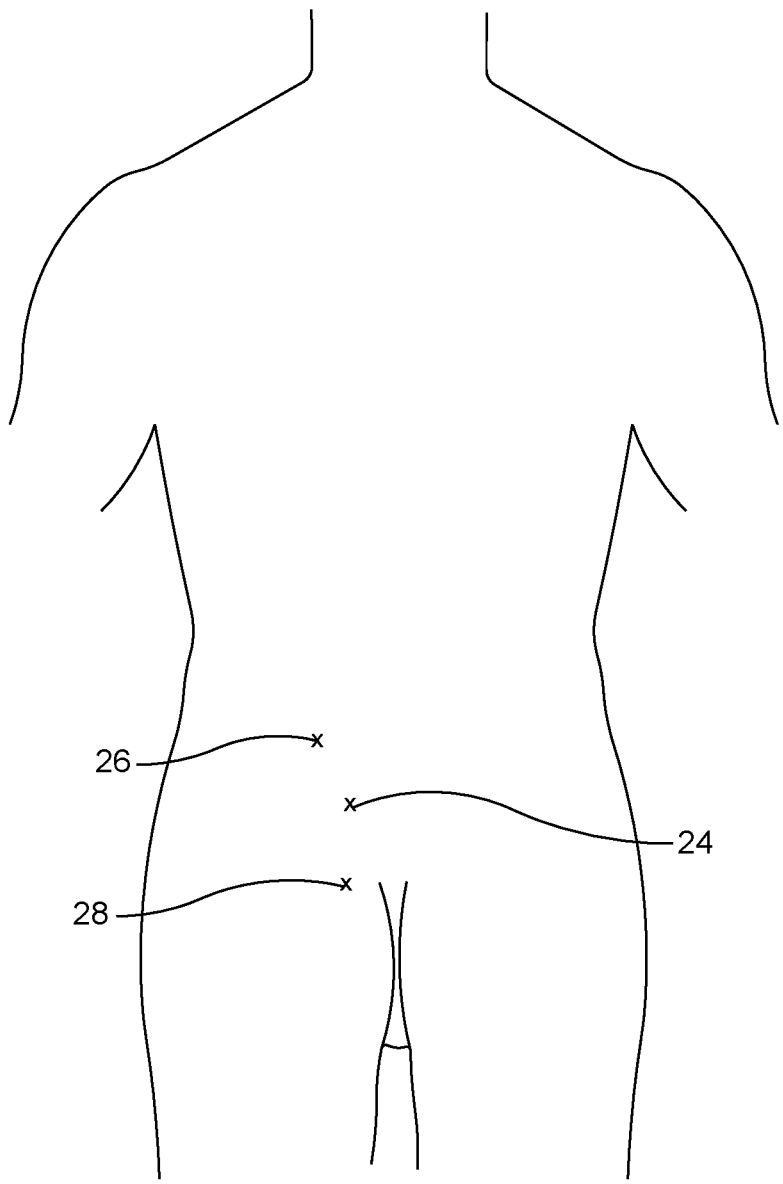
FIG. 4 is a diagrammatic view of three incision points that are marked on the patient's skin after the markings in FIGS. 1B, 2B, and 3B have been made.

Three incision points are then marked on the skin, as depicted in FIG. 4.

Center incision point 24 is midway between the points where the second and third lines 18 and 22 cross first line 12 and is spaced in the medial direction about three to five millimeters (3-5 mm) from first line 12.

Superior incision point 26 is spaced in the medial direction about three to five millimeters (3-5 mm) from the intersection of first line 12 and second line 14.

Inferior incision point 28 is spaced in the medial direction about three to five millimeters (3-5 mm) from the intersection of first line 12 and third line 22.

Figure 5:
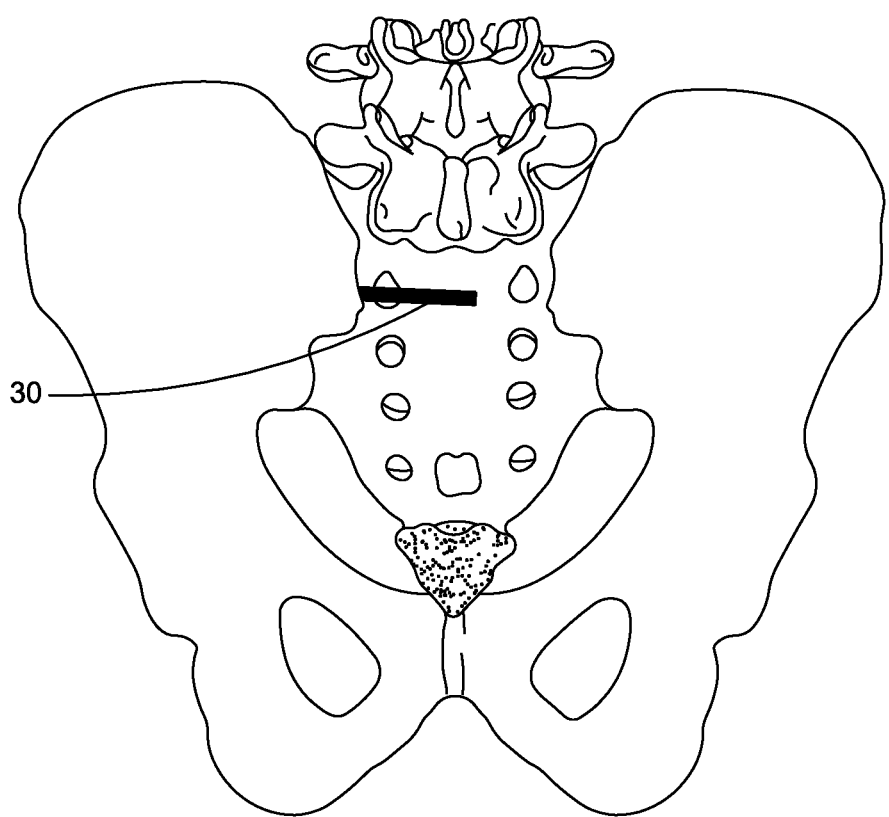
FIG. 5 is an X-ray view depicting a guide wire inserted through the central incision point of the three incision points of FIG. 4.

As depicted in FIG. 5, a fourth guide wire 30 is inserted through center incision point 24, with a superior/inferior angle perpendicular to the patient. The medial/lateral angle is the same as the oblique angle on the C-arm, which is approximately thirty-five degrees (35°). Fourth guide wire 30 is guided into the SI joint and an incision is made when guide wire 30 is properly positioned.

Figure 6A:
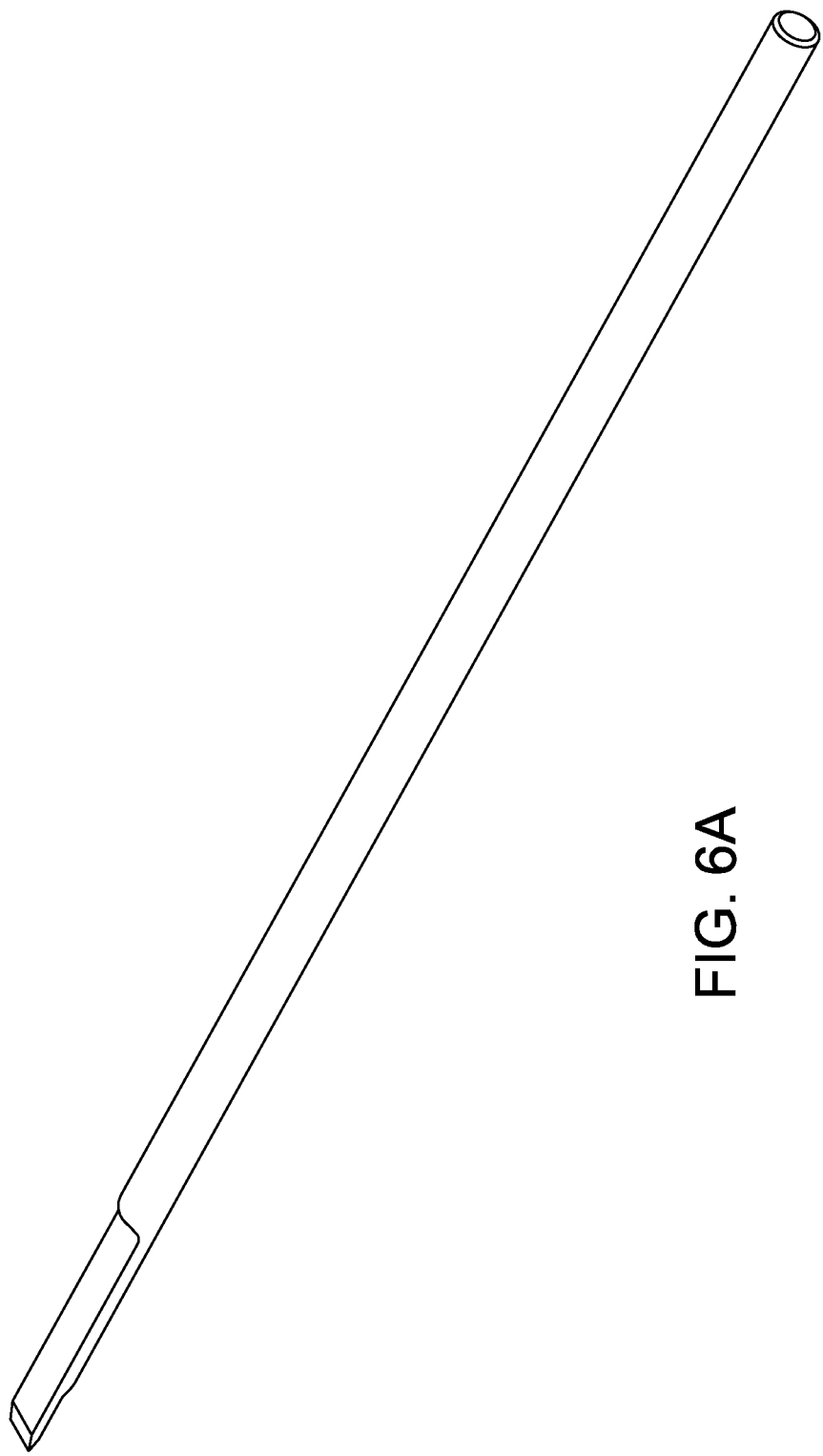
FIG. 6A is a perspective view of a joint locator.
Figure 6B:
FIG. 6B is a side elevational view of the joint locator.
Figure 6C:
FIG. 6C is a top plan view of the joint locator.

Joint locator 50, depicted in FIGS. 6A-C, is then placed over guide wire 30, i.e., in ensleeving relation to said guide wire 30. A surface of joint locater 50 is etched black and that black-etched surface is positioned so that it faces the ilium.

Directional cannula 52, depicted in FIGS. 7A-7G, is then placed over joint locator 50, i.e., in ensleeving relation to said joint locator. A surface of directional cannula 52 is etched black and that black-etched surface matches the black-etched surface of joint locator 50, i.e., the black-etched surface of directional cannula 52 is also positioned so that it faces the ilium.

Directional cannula 52 has a cylindrical main body 52a having longitudinally-extending central bore 52b formed therein. Central bore 52b has a transverse profile that matches the transverse profile of a fusion implant. A leading end of central bore 52b is exposed to view by cut-out or notch 52c. Two prongs 52d and 52e extend from said leading end in transversely spaced, parallel relation to one another. Prongs 52d and 52e enter the sacroiliac joint when directional cannula 52 is in use. Barb 52f is formed in the leading end of main body 52a as depicted in FIGS. 7B-7E. Barb 52f engages the sacrum to prevent slippage when prongs 52d and 52e enter into sacroiliac joint 10.

Figure 7A:
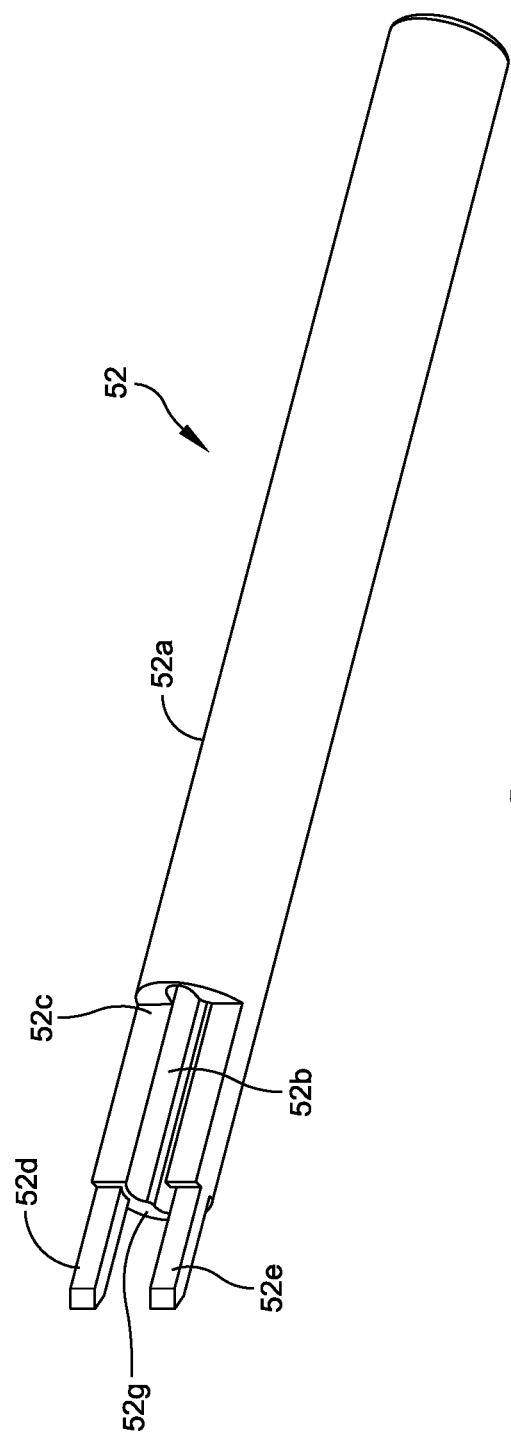
FIG. 7A is a perspective view of a novel directional cannula.
Figure 7B:
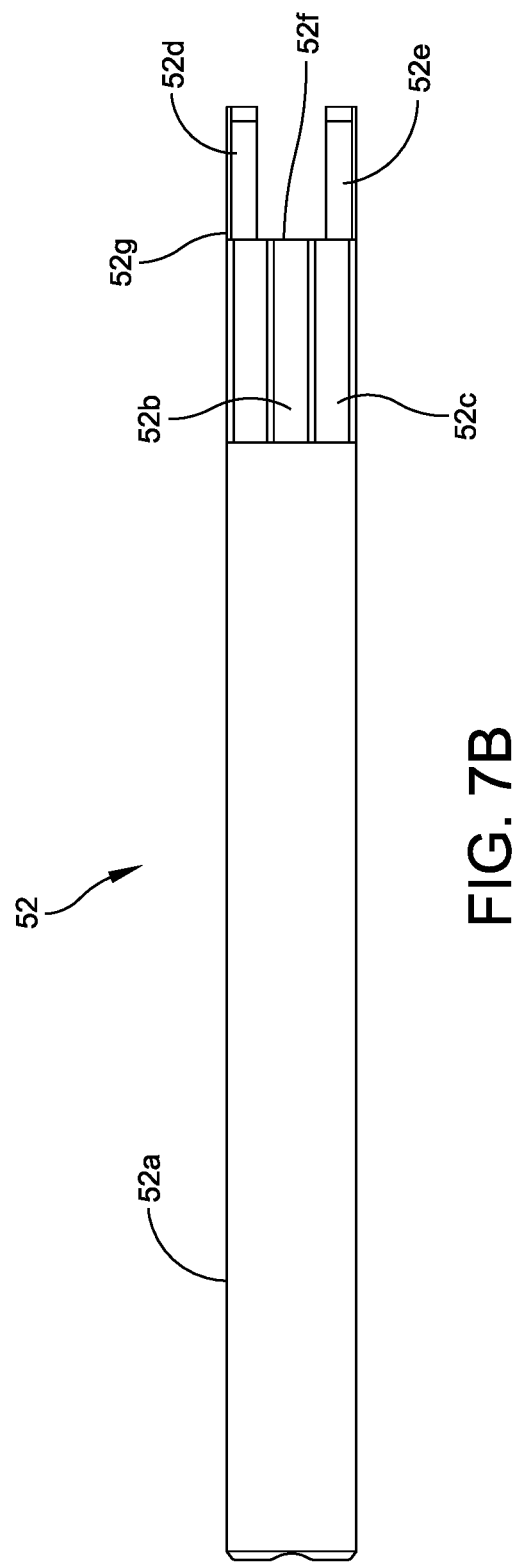
FIG. 7B is a top plan view of the directional cannula of FIG. 7A.
Figure 7F:
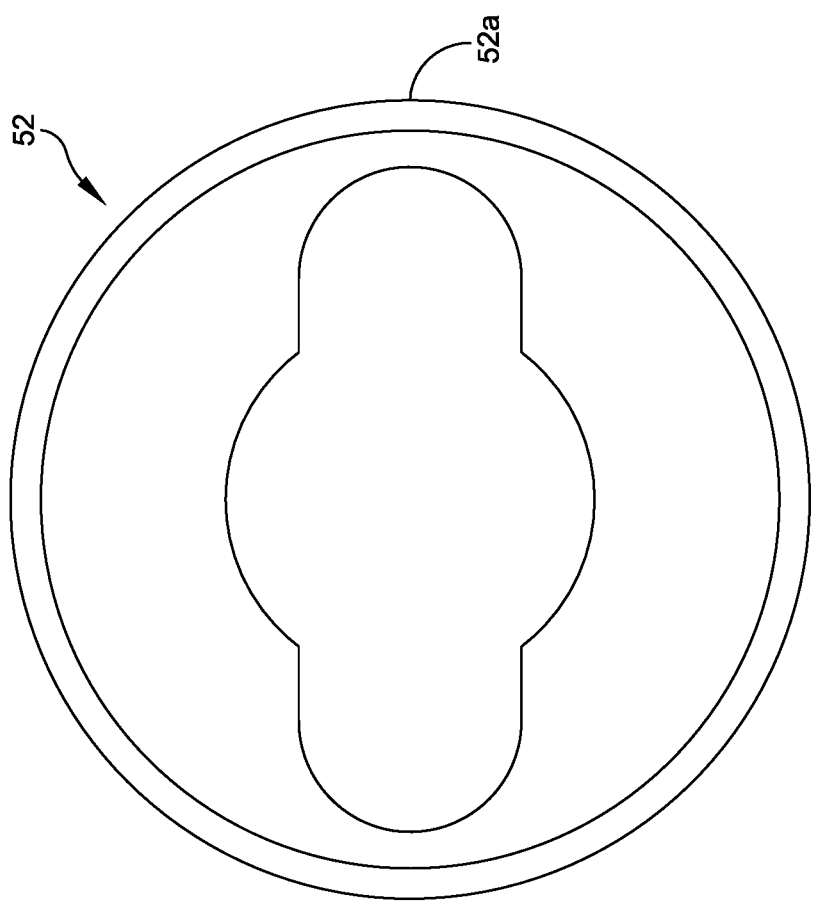
FIG. 7F is an end view of the trailing end of the directional cannula of FIG. 7A.
Figure 7H:
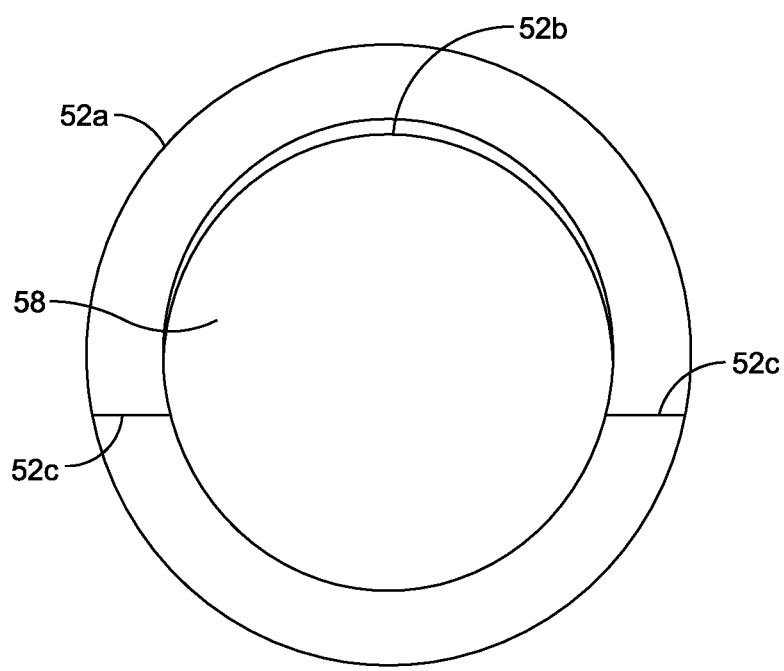
FIG. 7H is an end view taken along lines 7H-7H in FIG. 7G.
Figure 7G:
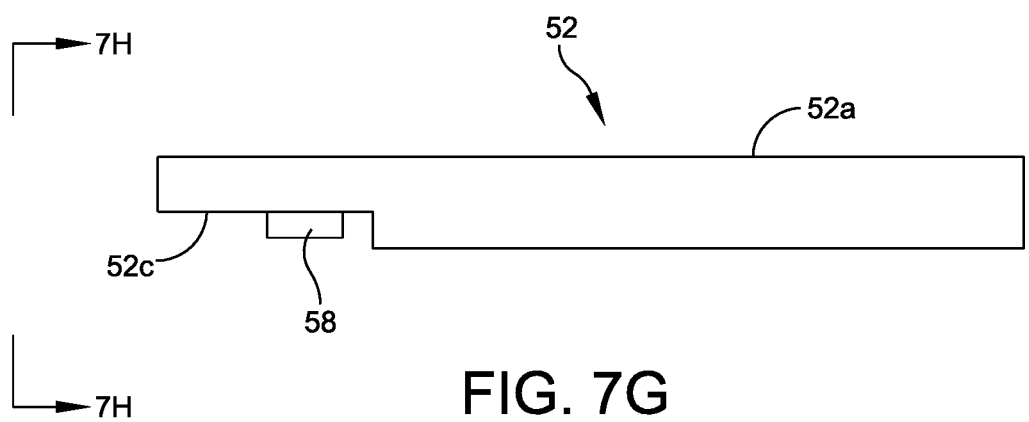
FIG. 7G is a side elevational view similar to FIG. 7C, but depicting an implant exposed to view by a notch but captured within a lumen so that it cannot fall.
Figure 8A:
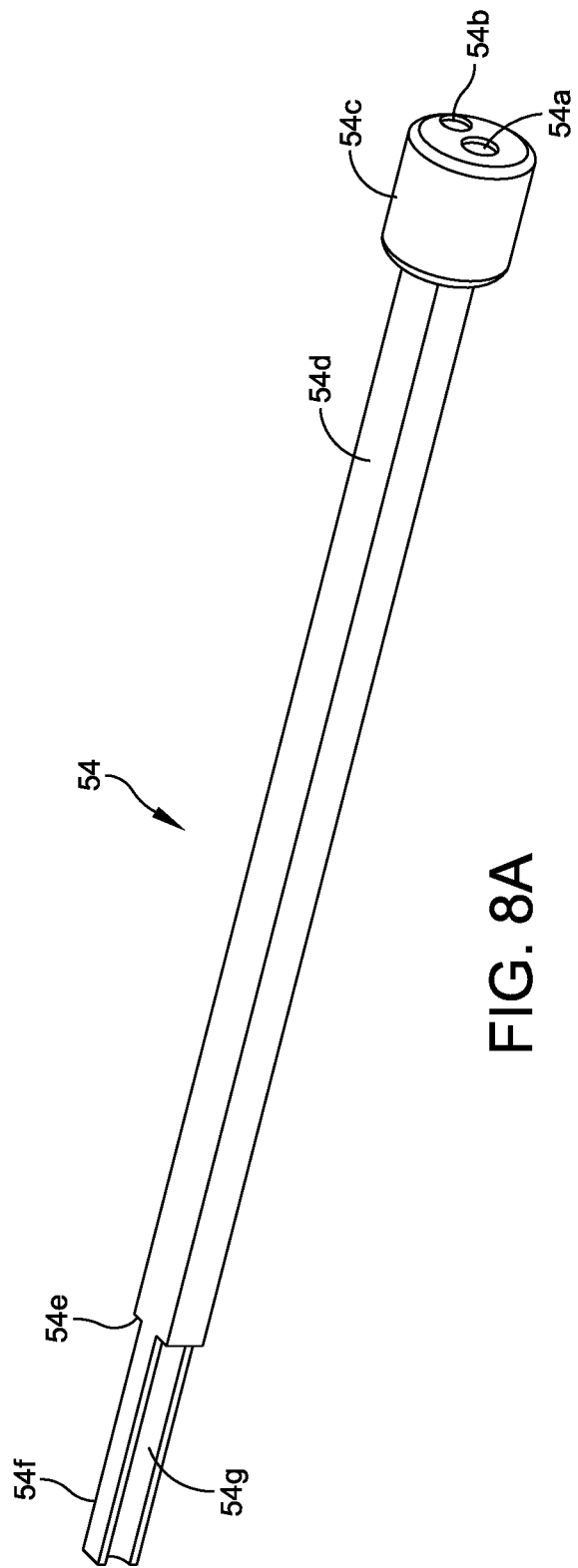
FIG. 8A is a perspective view of a novel drill guide.
Figure 8B:
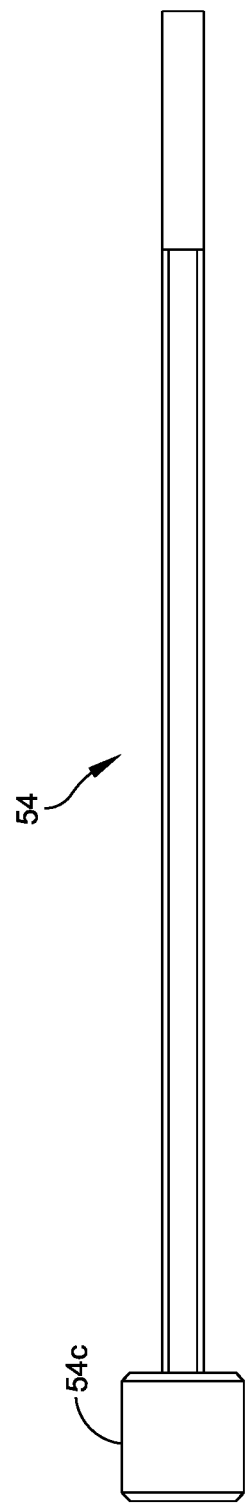
FIG. 8B is a side elevational view of the drill guide of FIG. 8A.
Figure 8C:
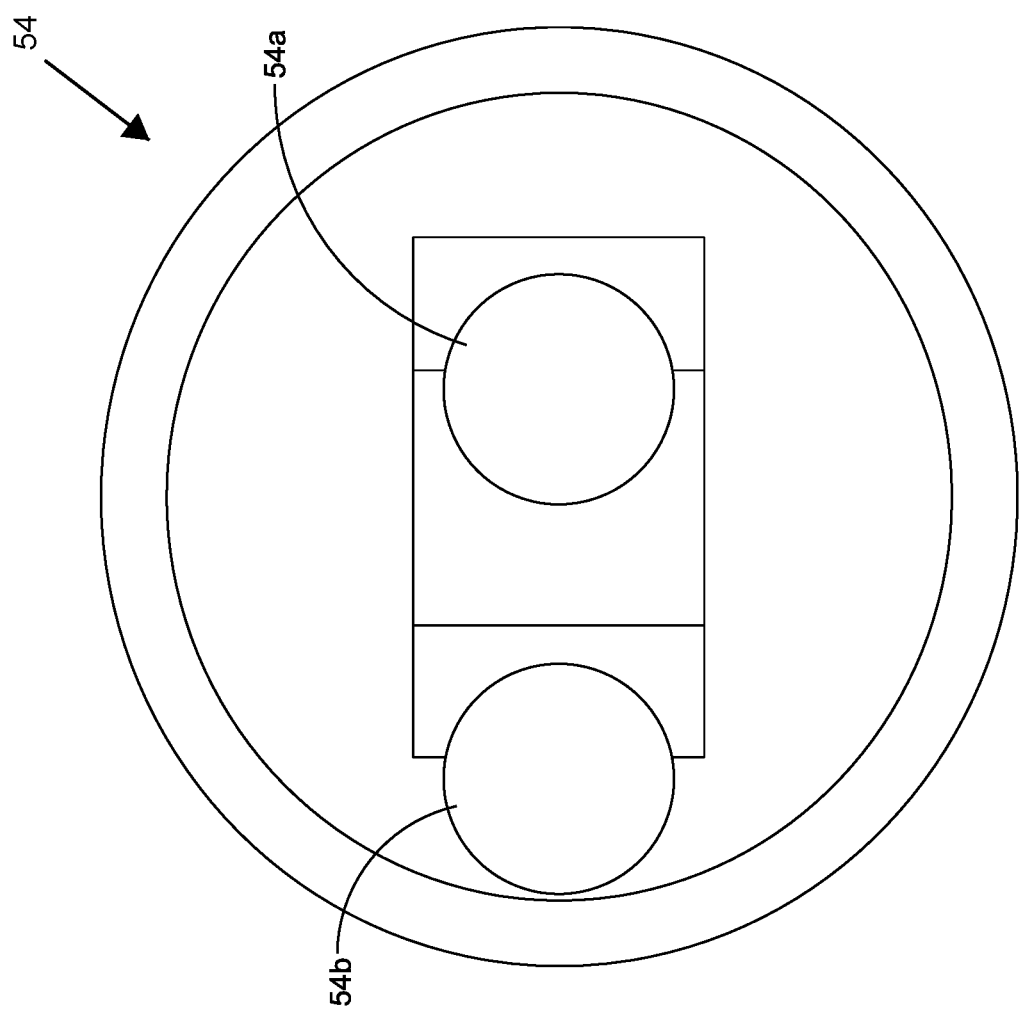
FIG. 8C is an end elevational view of the leading end of the drill guide of FIG. 8A.

FIG. 7G depicts implant 58 that is captured within bore 52b. Implant 58 is exposed to view because it is in the region of bore 52b where notch 52c is formed. Since the radial depth of notch 52c is less than half the diameter of bore 52b, implant 58 cannot fall from bore/lumen 52b. In other words, as indicated in FIG. 7H, notch 52c creates a "C"-shaped bore where the two (2) spaced apart points of the "C" are closer together than the widest part of implant 58, thereby retaining the implant within bore 52b.

Joint locator 50 and guide wire 30 are then retracted, leaving directional cannula 52 in position. When so positioned, prongs 52d, 52e are disposed in sacroiliac joint 10. Barb 52f engages the sacrum to hold directional cannula 52 in position as aforesaid.

Drill guide 54, depicted in FIGS. 8A-8D, has longitudinally extending eccentric bores 54a, 54b formed therein. Head 54c is enlarged relative to main body 54d that is rectangular in transverse section. Step 54e is formed where the transverse extent of main body 54d is reduced. Drill bit-accommodating semi-circular grooves 54f and 54g are the continuation of bores 54a, 54b and are formed in opposite sides of the leading end of drill guide 54, said leading end being the part of main body 54d that extends distal of said step 54e.

Drill guide 54 is inserted into the central bore or lumen of directional cannula 52 towards the sacrum to verify placement of directional cannula 52 into the SI joint. The lumen of directional cannula 52 has a profile that enables it to slidingly receive drill guide 54 in the center of the larger implant-receiving lumen.

Figure 9:
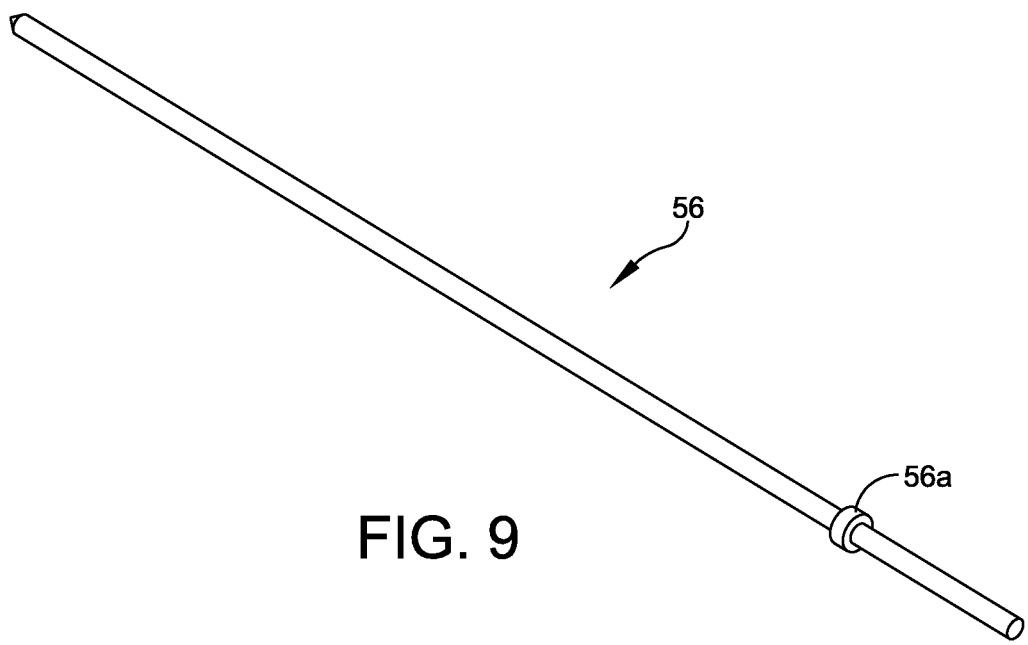
FIG. 9 is a perspective view of a drill bit.

Drill bit 56, depicted in FIG. 9, having positive stop 56a is then inserted into eccentric bore 54a and said drill bit 56 is slid towards the sacrum until it abuts the sacrum.

The distance from the proximal end of head 54c of drill guide 54 to the lower side of positive stop 56a is then measured. Directional cannula 52 is properly seated in the SI joint if the measured distance is between twenty-five to thirty millimeters (25-30 mm). The proper seating can also be confirmed with a lateral X-ray view that shows the leading end of directional cannula 52 disposed flush with the sacrum.

Drill bit 56 is then inserted into eccentric drill guide bore 54a and a first cavity is created in the ilium by a first drilling, until positive stop 56a abuts the proximal end of directional cannula 52. Drill bit 56 is then withdrawn from bore 54a, placed into bore 54b, and a second cavity is formed in the ilium by a second drilling. The second drilling continues until drill bit 56 reaches positive stop 56a.

Drill guide 54 is then retracted from directional cannula 52 and rotated one hundred eighty degrees (180°). Drill bit 56 is then inserted into eccentric drill guide bore 54a and a first cavity is created in the sacrum by a third drilling that continues until drill bit 56 reaches positive stop 56a. Drill bit 56 is then withdrawn from bore 54a, placed into bore 54b, and a second cavity is formed in the sacrum by a fourth drilling. The fourth drilling continues until drill bit 56 reaches positive stop 56a. Drill bit 56 is then removed.

Due to the eccentricity of the bores and the rotation of the drill guide, all four cavities merge into a single cavity that accommodates the fusion implant.

Figure 10:
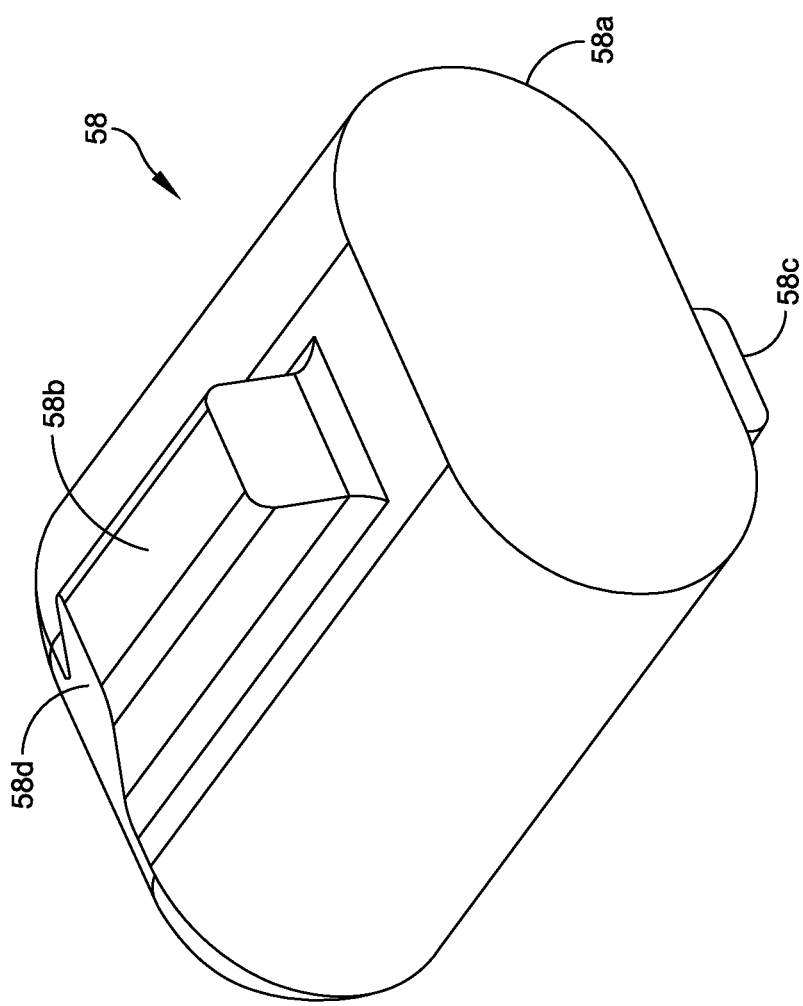
FIG. 10 is a perspective view of a fusion implant device.

When the drilling is completed, drill guide 54 is retracted from directional cannula 52 and fusion implant 58, depicted in FIG. 10, is inserted into the lumen of directional cannula 52. The chamfer is inserted downward.

Fusion implant 58 may take many forms and may be as simple as a dowel having a circular cross-section, i.e., the oval shape of main body 58a, upper and lower fins 58b, 58c, and the swept back leading edge 58d of said fins are not critical parts of the fusion implant.

Figure 11:
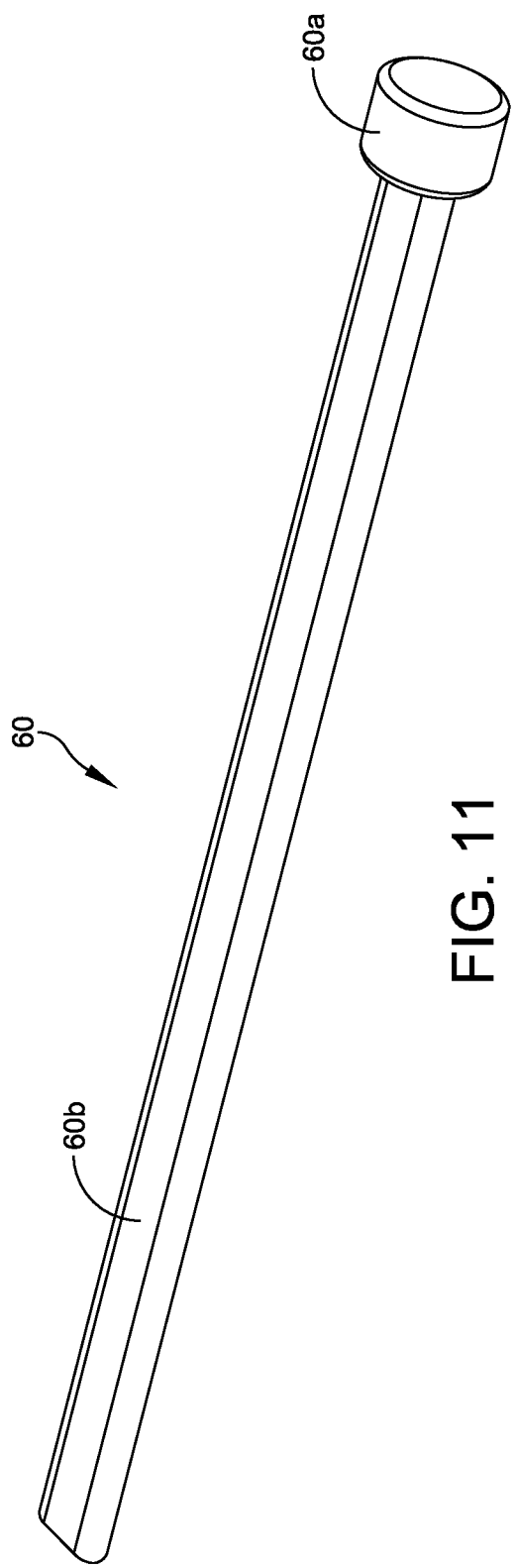
FIG. 11 is a perspective view of a tamp.

Implant tamp 60, depicted in FIG. 11, includes head 60a and flat, elongate main body 60b. A positive stop, not numbered, is formed where main body 60b meets head 60a. Main body 60b is inserted into the lumen of directional cannula 52 to advance the implant. Head 60a is repeatedly tamped lightly with a hammer or other suitable tool, not illustrated, until the aforesaid positive stop abuts directional cannula 52. This should fully seat implant 58 in the SI joint, i.e., implant 58 should be countersunk into the SI joint by a distance of about three to five millimeters (3-5 mm). A lateral X-ray view is taken to confirm full deployment of implant 58.

As perhaps best understood in connection with FIGS. 7B and 7C, implant 58 emerges from bore 52b at cut-out or notch 52c. Notch 52c has an extent or depth less than half the diameter of cylindrical main body 52a as depicted in FIGS. 7C and 7E. Implant 58 is thus supported from below by the part of main body 52a that is not removed to form notch 52c. The dimensions of implant 58 allow it to be inserted into bore 52b, but prevent it from falling out upon exiting bore 52b, i.e., upon exposure to or open communication with notch 52c, i.e., implant 58 is supported from below by the longitudinally-extending part of notch 52c as perhaps best understood in connection with FIG. 7C. Implant 58 is inside the cavity drilled into the sacrum and ilium when said implant extends beyond leading end 52g of cylindrical main body 52a.

A guide wire is then inserted through superior incision point 26 at a superior/interior angle about forty-five degrees (45°) towards superior. The medial/lateral angle is the same as the oblique angle on the C-arm, which is approximately thirty-five degrees (35°).

The guide wire is then guided into the SI joint. A second incision is made when the guide wire is properly positioned. The steps that follow the first incision are then repeated, i.e., joint locator 50 is inserted over the guide wire, directional cannula 52 is paced over the joint locator, and so on.

The procedure is concluded by inserting a guide wire through inferior incision point 28 at a superior/interior angle about forty-five degrees (45°) towards inferior. The medial/lateral angle is the same as the oblique angle on the C-arm, which is approximately thirty-five degrees (35°).

The guide wire is then guided into the SI joint. A third incision is made when the guide wire is properly positioned. The steps that follow the first and second incisions are then repeated, i.e., joint locator 50 is inserted over the guide wire, directional cannula 52 is paced over the joint locator, and so on.

Figure 12A:
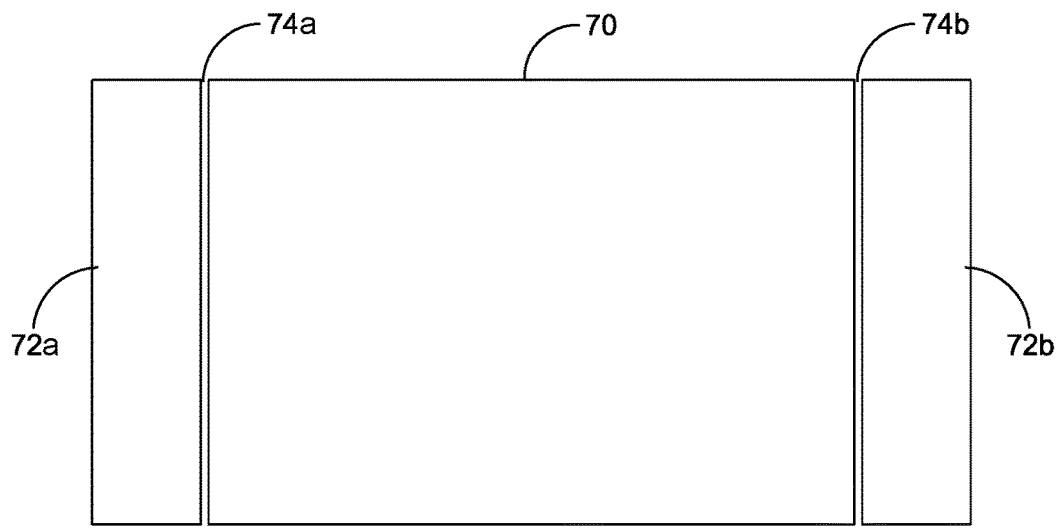
FIG. 12A is a front elevational diagrammatic representation of a sacrum flanked by a pair of iliums, showing two (2) sacroiliac joints.
Figure 12B:
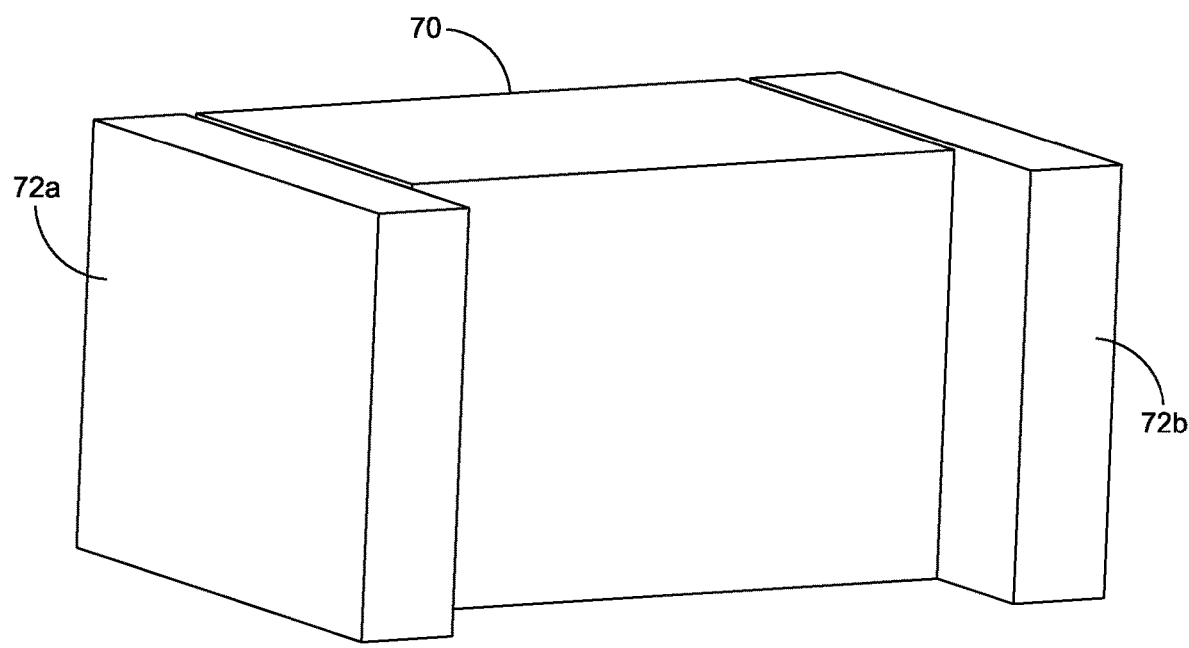
FIG. 12B is a first perspective view of the diagrammatic representation of FIG. 12A, indicating how the iliums protrude forwardly relative to the sacrum.
Figure 12C:
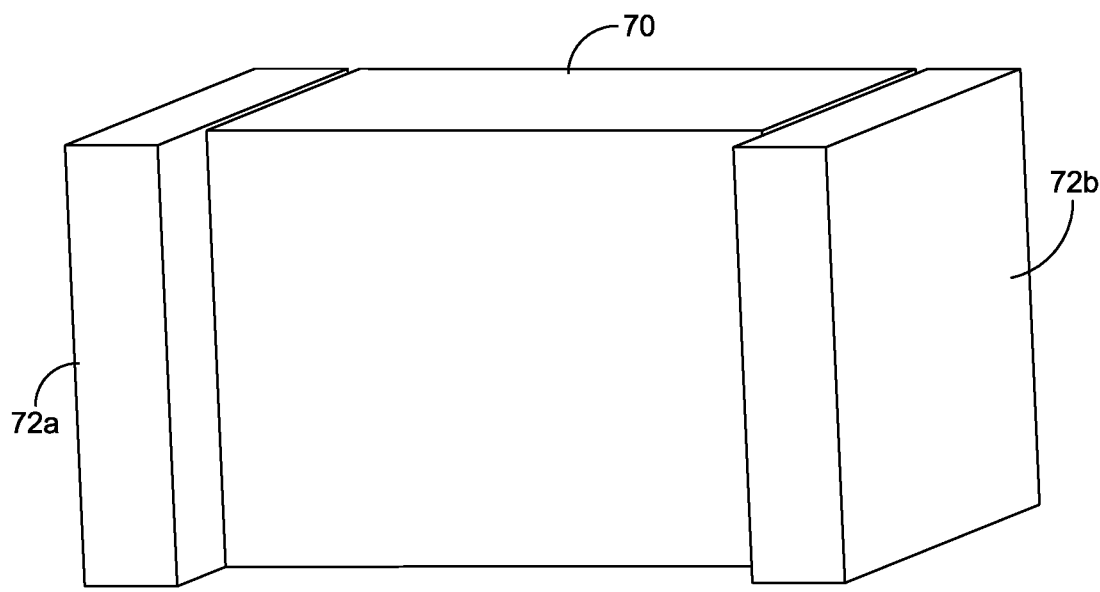
FIG. 12C is a second perspective view of the diagrammatic representation of FIG. 12A.
Figure 12D:
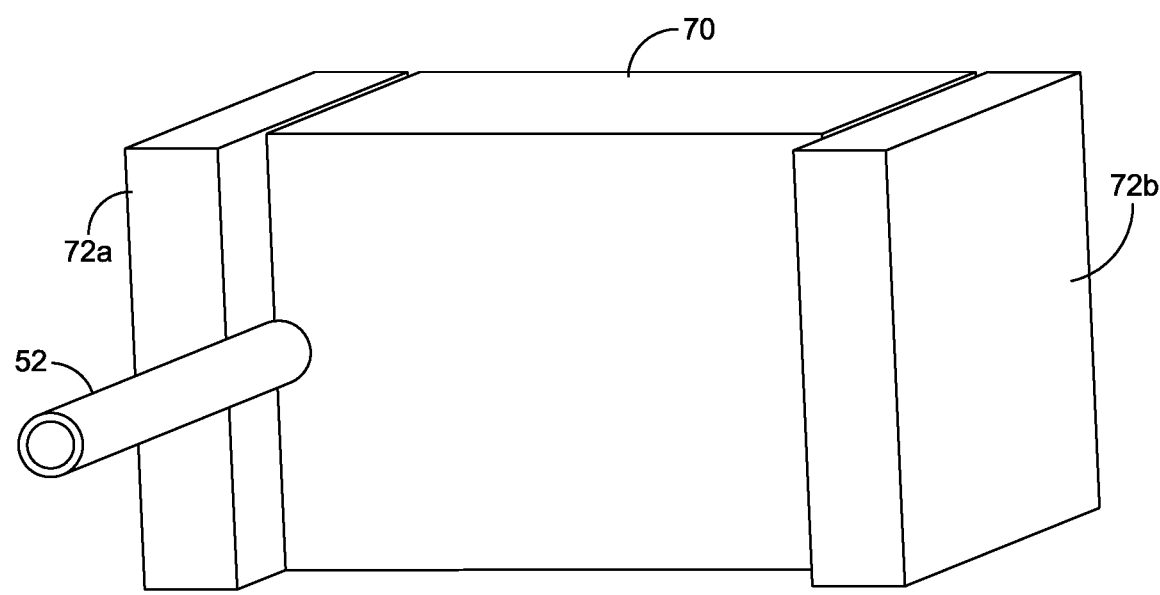
FIG. 12D is a view like FIG. 12C but adding a notched cannula, showing how the notch accommodates a protruding ilium.
Figure 12E:
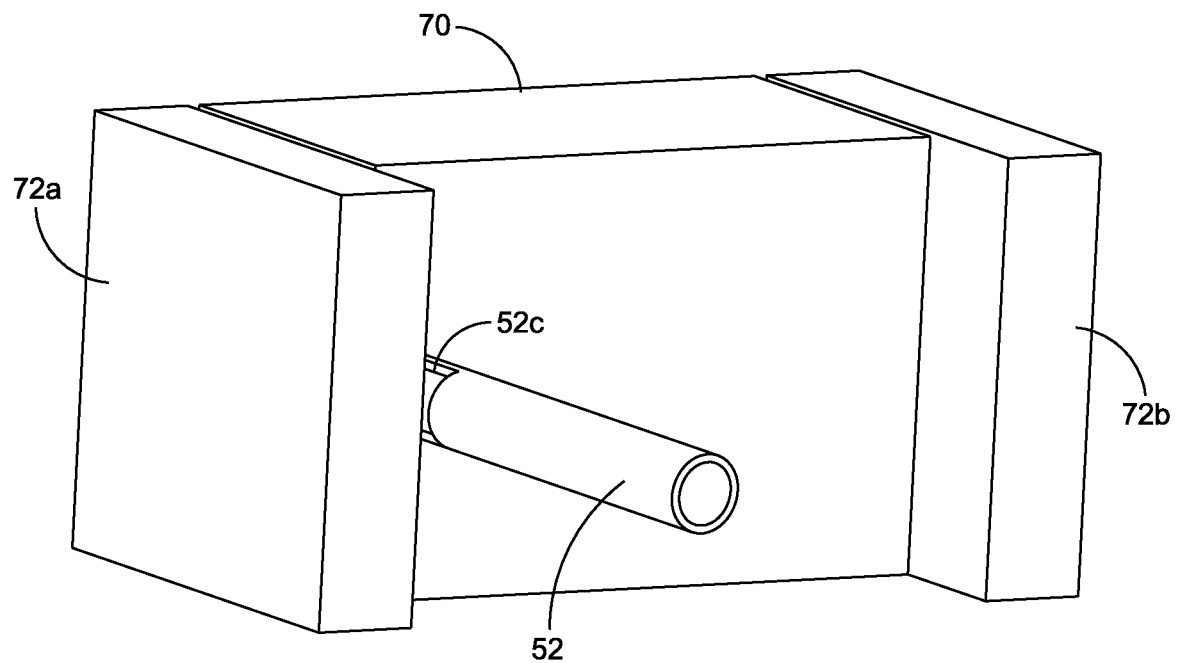
FIG. 12E depicts the same parts as FIG. 12D but taken from a left perspective.
Figure 12F:
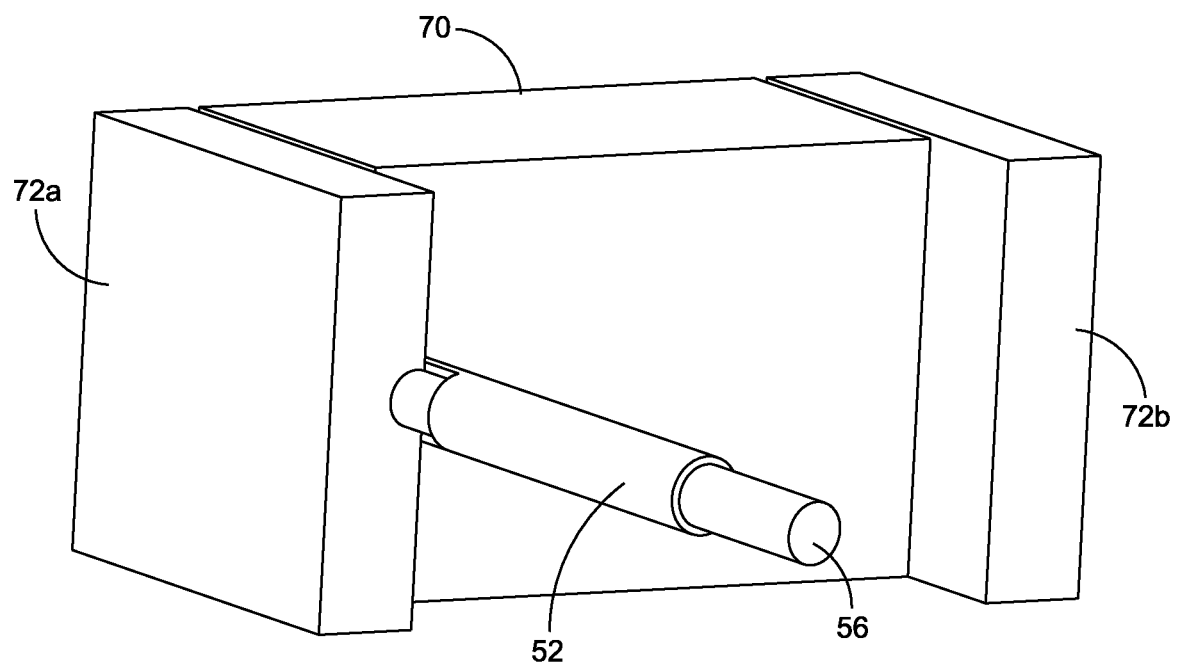
FIG. 12F is the same view as FIG. 12E but including the drill bit.
Figure 12G:
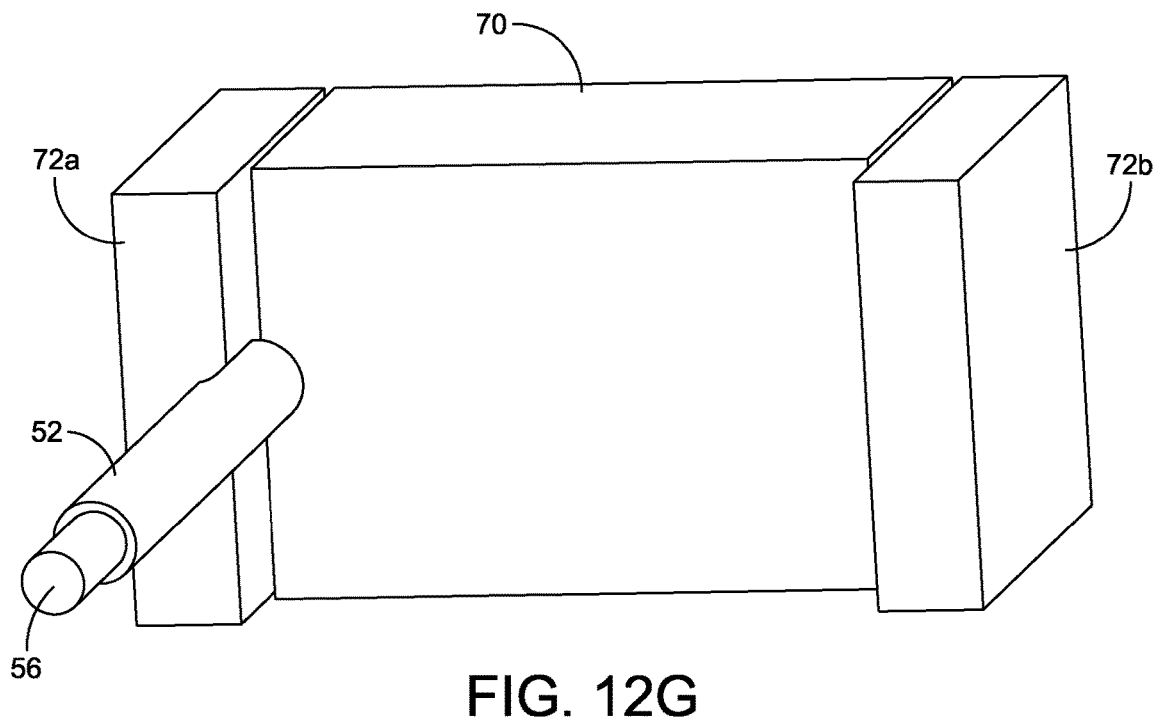
FIG. 12G is the same as FIG. 12F but taken from a right perspective.
Figure 12H:
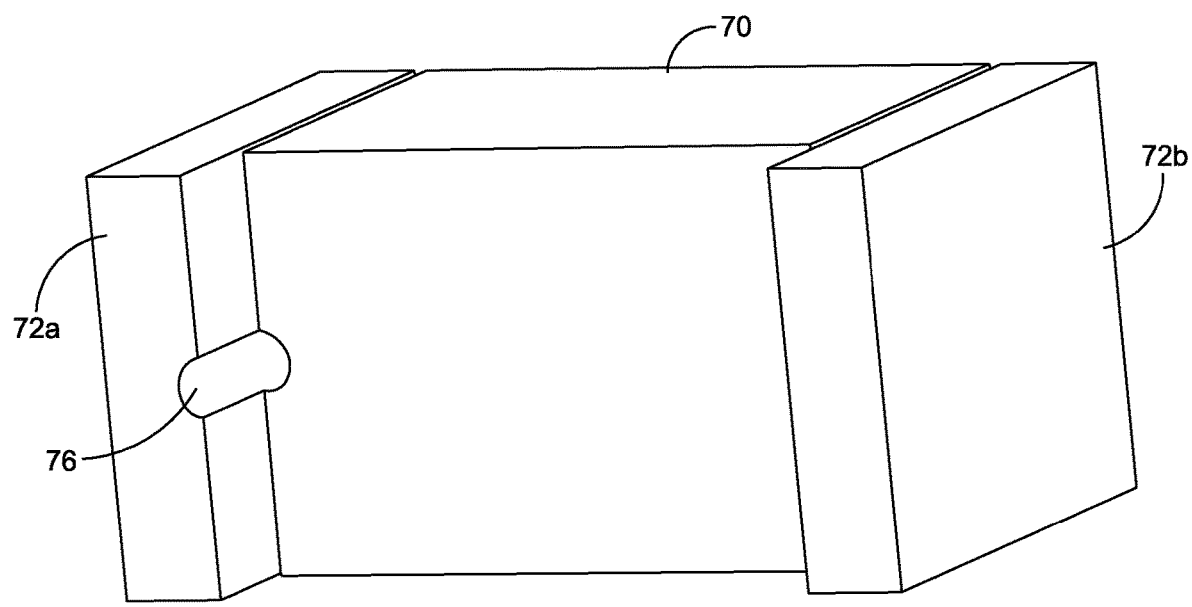
FIG. 12H depicts the cavity after drilling is complete and the cannula and drill bit have been withdrawn.
Figure 12I:
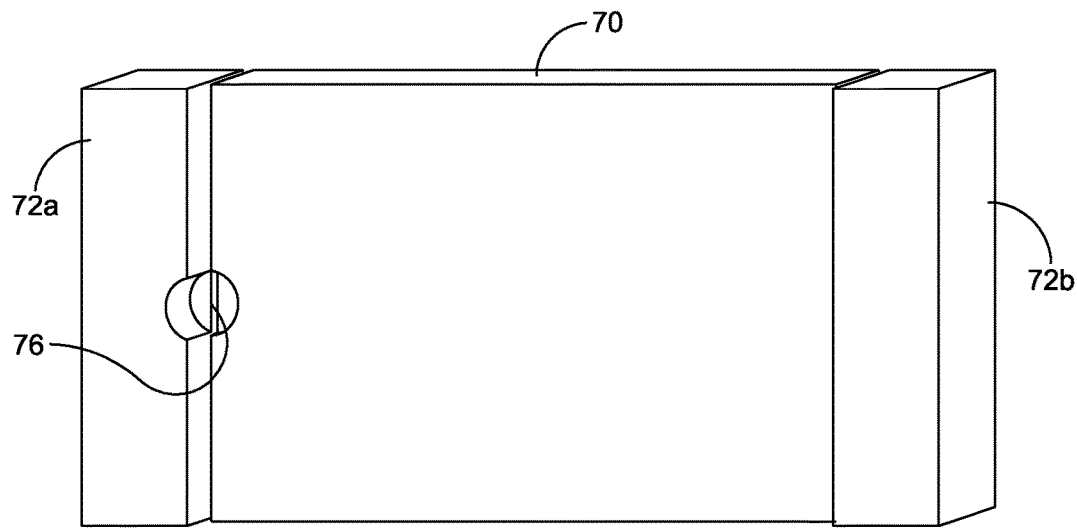
FIG. 12I is a like FIG. 12H but from a different perspective.
Figure 12J:
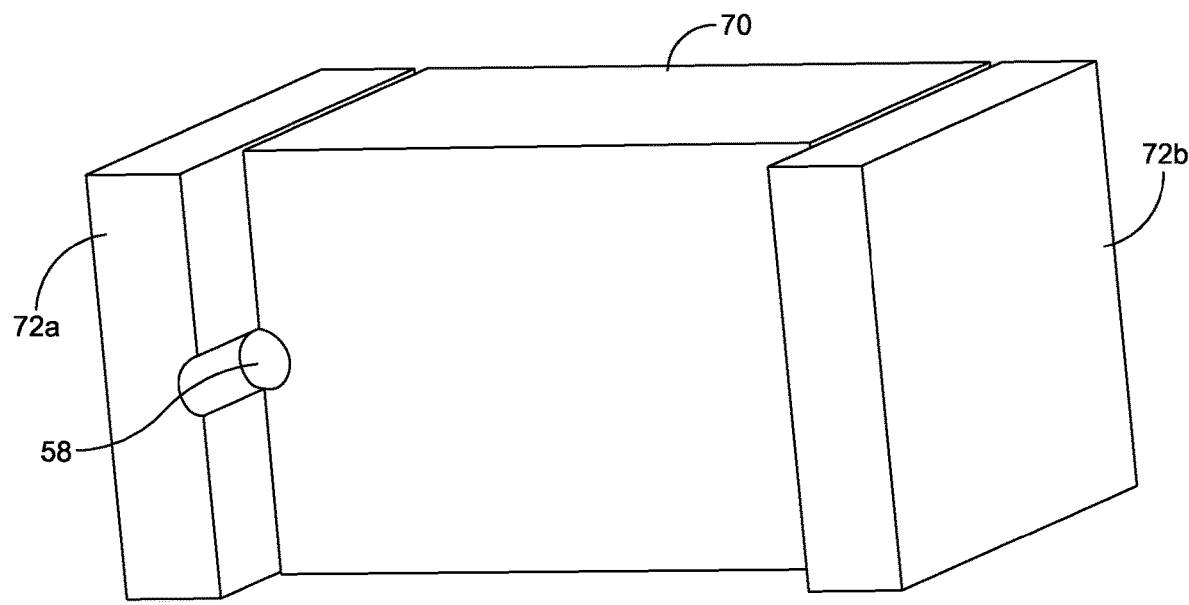
FIG. 12J depicts an implant in the drilled cavity.
Figure 12K:
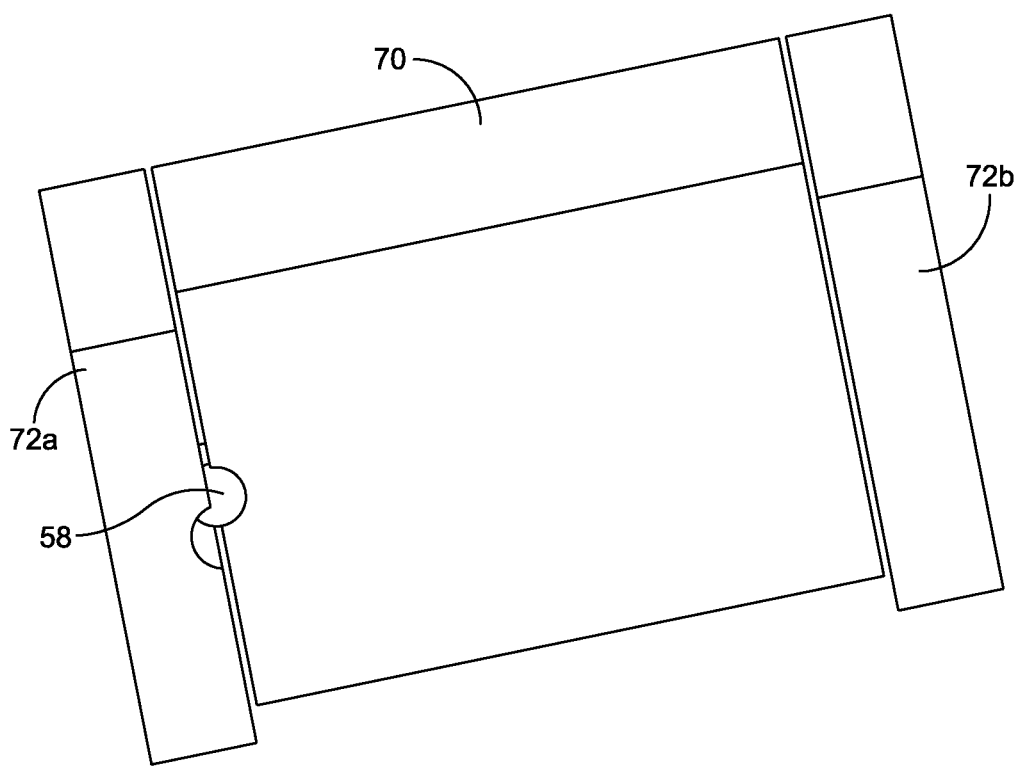
FIG. 12K depicts the same structure as FIG. 12J but from a different perspective.

FIGS. 12A-K provide a simplified overview of the procedure. FIG. 12A is a front elevational diagrammatic representation of a sacrum 70 flanked by a pair of iliums 72a, 72b, showing two (2) sacroiliac joints 74a, 74b and FIG. 12B is a first perspective view of the diagrammatic representation of FIG. 12A, indicating how iliums 72a, 72b protrude forwardly relative to sacrum 70. FIG. 12C is a second perspective view of the diagrammatic representation of FIG. 12A and FIG. 12D is a view like FIG. 12C but adding notched cannula 52, showing how notch 52c accommodates a protruding ilium. FIG. 12E depicts the same parts as FIG. 12D but taken from a left perspective and FIG. 12F is the same view as FIG. 12E but including drill bit 56. FIG. 12G is the same as FIG. 12F but taken from a right perspective. FIG. 12H depicts cavity 76 after drilling is complete and the cannula and drill bit have been withdrawn. FIG. 12I is a like FIG. 12H but from a different perspective, FIG. 12J depicts implant 58 in drilled cavity 76, and FIG. 12K depicts the same structure as FIG. 12J but from a different perspective.

It will thus be seen that the objects set forth above, and those made apparent from the foregoing disclosure, are efficiently attained and since certain changes may be made in the above construction without departing from the scope of the invention, it is intended that all matters contained in the foregoing disclosure or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A system for delivering an implant to a sacroiliac joint located between a sacrum and an ilium, said system comprising:
    an implant comprising an arcuate side wall and a non-circular transverse profile; and
    a cannula, said cannula comprising:
        an elongated body comprising a distal end terminating in a distal end surface, a proximal end, and a longitudinally-extending bore extending between the distal end surface and the proximal end, said bore defining a central longitudinal axis of said elongated body, wherein said distal end surface comprises a first generally planar surface defined by a plane transverse to said central longitudinal axis, said first generally planar surface being configured to seat securely against the sacrum; and
        a pair of diametrically-opposed prongs extending distally from said distal end surface of said elongated body, said pair of diametrically-opposed prongs being aligned along a prong axis which is parallel to the central longitudinal axis of said elongated body, said prongs being configured to enter the sacroiliac joint between the sacrum and the ilium;
    wherein said distal end of said elongated body comprises
        (i) an intermediate surface extending perpendicular to said central longitudinal axis of said elongated body, wherein said intermediate surface has a length that is less than half of a diameter of said elongated body, and
        (ii) a pair of side surfaces extending parallel to said central longitudinal axis of said elongated body from said distal end surface of said elongated body to said intermediate surface, wherein said intermediate surface comprises a second generally planar surface defined by a plane transverse to said central longitudinal axis, said second generally planar surface being configured to seat securely against the ilium.

2. The system of claim 1 wherein said implant has a cross-section comprising two arcuate portions connected by two generally linear portions.

3. The system of claim 1 wherein said implant comprises a circular cross-section.

4. The system of claim 1 wherein said implant comprises a main body, an upper fin disposed on an upper portion said main body, and a lower fin disposed on a lower portion of said main body.

5. The system of claim 1 wherein said longitudinally-extending bore of said elongated body comprises a transverse profile characterized by a first lateral dimension and a second lateral dimension disposed perpendicular to said first lateral dimension, wherein said first lateral dimension is larger than said second lateral dimension.

* * * * *